United States Patent
Gross

(10) Patent No.: US 9,770,593 B2
(45) Date of Patent: Sep. 26, 2017

(54) PATIENT SELECTION USING A TRANSLUMINALLY-APPLIED ELECTRIC CURRENT

(71) Applicant: RAINBOW MEDICAL LTD., Herzeliya (IL)

(72) Inventor: Yossi Gross, Moshav Mazor (IL)

(73) Assignee: PYTHAGORAS MEDICAL LTD., Herzliya (IL)

( * ) Notice: Subject to any disclaimer, the term of this patent is extended or adjusted under 35 U.S.C. 154(b) by 263 days.

(21) Appl. No.: 13/771,853

(22) Filed: Feb. 20, 2013

(65) Prior Publication Data

US 2014/0128865 A1    May 8, 2014

Related U.S. Application Data

(60) Provisional application No. 61/722,293, filed on Nov. 5, 2012.

(51) Int. Cl.
*A61B 18/00* (2006.01)
*A61N 1/36* (2006.01)
(Continued)

(52) U.S. Cl.
CPC ........ *A61N 1/36114* (2013.01); *A61B 5/6876* (2013.01); *A61B 18/1492* (2013.01);
(Continued)

(58) Field of Classification Search
CPC ...... A61B 18/1492; A61B 2018/00577; A61B 2018/00404; A61B 2018/00511;
(Continued)

(56) References Cited

U.S. PATENT DOCUMENTS

| 4,106,488 A | 8/1978 | Gordon |
| 4,569,836 A | 2/1986 | Gordon |

(Continued)

FOREIGN PATENT DOCUMENTS

| CN | 102551878 | 7/2012 |
| CN | 203089369 U | 7/2013 |

(Continued)

OTHER PUBLICATIONS

Buch E et al., "Intra-pericardial balloon retraction of the left atrium: A novel method to prevent esophageal injury during catheter ablation," Heart Rhythm 2008;5:1473-1475.

(Continued)

*Primary Examiner* — Christopher D Koharski
*Assistant Examiner* — Pamela M Bays
(74) *Attorney, Agent, or Firm* — Sughrue Mion, PLLC

(57) ABSTRACT

Apparatus for facilitating ablation of nerve tissue of a subject is provided, comprising (1) an ablation unit, configured to be percutaneously advanced to a site adjacent to a first portion of the nerve tissue; (2) at least one electrode unit, coupled to the ablation unit, and configured to be percutaneously advanced to a site adjacent to a second portion of the nerve tissue, and to initiate unidirectional action potentials in the nerve tissue, such that the unidirectional action potentials propagate toward the first portion of the nerve tissue; and (3) a control unit, configured: (a) to drive the ablation unit to ablate, at least in part, the first portion of the nerve tissue of the subject, and (b) to drive the at least one electrode unit to initiate the unidirectional action potentials by applying an excitatory current to the second portion of the nerve tissue.

7 Claims, 13 Drawing Sheets

(51) Int. Cl.
   *A61B 5/00*    (2006.01)
   *A61B 18/14*   (2006.01)
   *A61F 2/06*    (2013.01)
   *A61N 1/05*    (2006.01)

(52) U.S. Cl.
   CPC .............. *A61B 2018/00214* (2013.01); *A61B 2018/00404* (2013.01); *A61B 2018/00434* (2013.01); *A61B 2018/00511* (2013.01); *A61B 2018/00577* (2013.01); *A61B 2018/1407* (2013.01); *A61F 2/06* (2013.01); *A61N 1/0514* (2013.01)

(58) Field of Classification Search
   CPC ..... A61B 5/6876; A61F 2/06; A61N 1/36114; A61N 1/0514
   USPC ........................................... 606/41; 607/118
   See application file for complete search history.

(56) References Cited

U.S. PATENT DOCUMENTS

| | | |
|---|---|---|
| 4,619,247 A | 10/1986 | Inoue |
| 5,697,377 A | 12/1997 | Wittkampf |
| 5,735,280 A | 4/1998 | Sherman et al. |
| 5,776,063 A | 7/1998 | Dittrich et al. |
| 5,807,285 A | 9/1998 | Vaitekunas |
| 5,817,022 A | 10/1998 | Vesely |
| 5,827,216 A | 10/1998 | Igo et al. |
| 6,050,943 A | 4/2000 | Slayton |
| 6,064,902 A | 5/2000 | Haissaguerre et al. |
| 6,117,101 A | 9/2000 | Diederich |
| 6,128,523 A | 10/2000 | Bechtold |
| 6,161,048 A | 12/2000 | Sluijter |
| 6,219,577 B1 | 4/2001 | Brown |
| 6,233,477 B1 | 5/2001 | Chia |
| 6,241,727 B1 | 6/2001 | Tu |
| 6,246,899 B1 | 6/2001 | Chia |
| 6,361,500 B1 | 3/2002 | Masters |
| 6,405,732 B1 | 6/2002 | Edwards |
| 6,425,877 B1 | 7/2002 | Edwards |
| 6,440,077 B1 | 8/2002 | Jung |
| 6,522,926 B1 | 2/2003 | Kieval |
| 6,526,318 B1 | 2/2003 | Ansarinia |
| 6,605,084 B2 | 8/2003 | Acker et al. |
| 6,635,054 B2 | 10/2003 | Fjield et al. |
| 6,641,579 B1 | 11/2003 | Bernardi |
| 6,659,950 B2 | 12/2003 | Taheri |
| 6,685,639 B1 | 2/2004 | Wang |
| 6,692,490 B1 | 2/2004 | Edwards |
| 6,701,931 B2 | 3/2004 | Sliwa et al. |
| 6,736,835 B2 | 5/2004 | Pellegrino |
| 6,740,040 B1 | 5/2004 | Mandrusov |
| 6,805,129 B1 | 10/2004 | Pless et al. |
| 6,845,267 B2 | 1/2005 | Harrison |
| 7,001,336 B2 | 2/2006 | Mandrusov |
| 7,022,105 B1 | 4/2006 | Edwards |
| 7,037,306 B2 | 5/2006 | Podany et al. |
| 7,149,574 B2 | 12/2006 | Yun |
| 7,162,303 B2 | 1/2007 | Levin |
| 7,226,440 B2 | 6/2007 | Gelfand et al. |
| 7,311,701 B2 | 12/2007 | Gifford et al. |
| 7,326,201 B2 | 2/2008 | Fjield et al. |
| 7,430,449 B2 | 9/2008 | Aldrich |
| 7,499,747 B2 | 3/2009 | Kieval |
| 7,510,536 B2 | 3/2009 | Foley |
| 7,553,284 B2 | 6/2009 | Vaitekunas |
| 7,565,191 B2 | 7/2009 | Burbank et al. |
| 7,617,005 B2 | 11/2009 | Demarais |
| 7,653,438 B2 | 1/2010 | Deem |
| 7,662,099 B2 | 2/2010 | Podany et al. |
| 7,684,865 B2 | 3/2010 | Aldrich |
| 7,706,882 B2 | 4/2010 | Franischelli |
| 7,717,948 B2 | 5/2010 | Demarais |
| 7,840,271 B2 | 11/2010 | Kieval |
| 7,853,333 B2 | 12/2010 | Demarais |
| 7,854,733 B2 | 12/2010 | Govari |
| 7,901,359 B2 | 3/2011 | Mandrusov |
| 7,974,696 B1 | 7/2011 | DiLorenzo |
| 8,197,409 B2 | 6/2012 | Foley |
| 8,391,970 B2 | 3/2013 | Tracey et al. |
| 8,585,601 B2 | 11/2013 | Sverdlik et al. |
| 8,696,581 B2 | 4/2014 | Sverdlik et al. |
| 8,702,619 B2 | 4/2014 | Wang |
| 9,014,821 B2 | 4/2015 | Wang |
| 9,028,417 B2 | 5/2015 | Sverdlik et al. |
| 9,566,456 B2 | 2/2017 | Sverdlik et al. |
| 2001/0003798 A1 | 6/2001 | McGovern |
| 2001/0007940 A1 | 7/2001 | Tu |
| 2002/0091427 A1 | 7/2002 | Rappaport |
| 2002/0147446 A1 | 10/2002 | Ein-Gal |
| 2002/0173688 A1 | 11/2002 | Chen |
| 2003/0013968 A1 | 1/2003 | Fjield |
| 2003/0018256 A1 | 1/2003 | Sasaki |
| 2003/0045909 A1* | 3/2003 | Gross et al. ..................... 607/9 |
| 2003/0055421 A1 | 3/2003 | West |
| 2003/0069590 A1 | 4/2003 | Rabiner |
| 2004/0034339 A1 | 2/2004 | Stoller |
| 2004/0038857 A1 | 2/2004 | Tracey |
| 2004/0097788 A1 | 5/2004 | Mourlas |
| 2004/0122494 A1 | 6/2004 | Eggers et al. |
| 2004/0162507 A1 | 8/2004 | Govari et al. |
| 2004/0162550 A1 | 8/2004 | Govari et al. |
| 2004/0193021 A1 | 9/2004 | Savage |
| 2005/0020921 A1 | 1/2005 | Glassell |
| 2005/0080469 A1 | 4/2005 | Larson et al. |
| 2005/0165298 A1 | 7/2005 | Larson |
| 2005/0192638 A1 | 9/2005 | Gelfand |
| 2005/0203410 A1 | 9/2005 | Jenkins |
| 2005/0251125 A1 | 11/2005 | Pless |
| 2005/0288651 A1 | 12/2005 | VanTassel et al. |
| 2006/0009753 A1 | 1/2006 | Fjield et al. |
| 2006/0041277 A1 | 2/2006 | Deem |
| 2006/0058711 A1 | 3/2006 | Harhen et al. |
| 2006/0100514 A1 | 5/2006 | Lopath |
| 2006/0184048 A1 | 8/2006 | Saadat |
| 2006/0206150 A1 | 9/2006 | Demarais |
| 2006/0212076 A1 | 9/2006 | Demarais |
| 2006/0212078 A1 | 9/2006 | Demarais |
| 2006/0241523 A1 | 10/2006 | Sinelnikov et al. |
| 2006/0265014 A1 | 11/2006 | Demarais |
| 2006/0265015 A1 | 11/2006 | Demarais |
| 2006/0271111 A1 | 11/2006 | Demarais |
| 2006/0276852 A1 | 12/2006 | Demarais |
| 2006/0287648 A1 | 12/2006 | Schwartz |
| 2007/0004984 A1 | 1/2007 | Crum et al. |
| 2007/0021803 A1 | 1/2007 | Deem |
| 2007/0038259 A1 | 2/2007 | Kieval |
| 2007/0060972 A1 | 3/2007 | Kieval |
| 2007/0093420 A1 | 4/2007 | Yeomans |
| 2007/0112327 A1 | 5/2007 | Lee |
| 2007/0129760 A1 | 6/2007 | Demarais |
| 2007/0129761 A1 | 6/2007 | Demarais |
| 2007/0135875 A1* | 6/2007 | Demarais ................ A61F 7/123 607/96 |
| 2007/0142879 A1 | 6/2007 | Greenberg |
| 2007/0162085 A1 | 7/2007 | DiLorenzo |
| 2007/0167984 A1 | 7/2007 | Kieval |
| 2007/0173899 A1* | 7/2007 | Levin ................ A61M 5/14276 607/40 |
| 2007/0191906 A1 | 8/2007 | Caparso |
| 2007/0203549 A1 | 8/2007 | Demarais |
| 2007/0239077 A1 | 10/2007 | Azhari et al. |
| 2007/0265610 A1 | 11/2007 | Thapliyal et al. |
| 2007/0265687 A1* | 11/2007 | Deem ................ A61B 18/1492 607/72 |
| 2007/0282407 A1 | 12/2007 | Demarais |
| 2008/0004614 A1 | 1/2008 | Burdette |
| 2008/0015445 A1 | 1/2008 | Saadat |
| 2008/0033415 A1 | 2/2008 | Rieker et al. |
| 2008/0039746 A1 | 2/2008 | Franischelli |
| 2008/0058682 A1 | 3/2008 | Azhari et al. |
| 2008/0058702 A1 | 3/2008 | Arndt |
| 2008/0071173 A1 | 3/2008 | Aldrich |

(56) References Cited

U.S. PATENT DOCUMENTS

| | | |
|---|---|---|
| 2008/0091109 A1 | 4/2008 | Abraham |
| 2008/0108984 A1 | 5/2008 | Burdette |
| 2008/0125819 A1 | 5/2008 | Ben-David et al. |
| 2008/0172104 A1 | 7/2008 | Kieval |
| 2008/0183248 A1 | 7/2008 | Rezai |
| 2008/0215111 A1 | 9/2008 | Kieval |
| 2008/0255449 A1 | 10/2008 | Sinelnikov |
| 2008/0255642 A1* | 10/2008 | Zarins ............... A61B 18/1206 607/99 |
| 2008/0281379 A1 | 11/2008 | Wesselink |
| 2008/0288017 A1 | 11/2008 | Kieval |
| 2008/0288031 A1 | 11/2008 | Wesselink |
| 2008/0306570 A1 | 12/2008 | Rezai |
| 2008/0319513 A1 | 12/2008 | Pu |
| 2009/0024195 A1 | 1/2009 | Rezai |
| 2009/0048514 A1 | 2/2009 | Azhari |
| 2009/0062790 A1 | 3/2009 | Malchano |
| 2009/0062873 A1 | 3/2009 | Wu |
| 2009/0076409 A1 | 3/2009 | Wu |
| 2009/0112133 A1 | 4/2009 | Deisseroth |
| 2009/0118780 A1 | 5/2009 | DiLorenzo |
| 2009/0137900 A1 | 5/2009 | Bonner et al. |
| 2009/0155336 A1 | 6/2009 | Rezai |
| 2009/0187230 A1 | 7/2009 | DiLorenzo |
| 2009/0192506 A9 | 7/2009 | Vaska et al. |
| 2009/0234407 A1* | 9/2009 | Hastings et al. .............. 607/14 |
| 2009/0247912 A1 | 10/2009 | Warnking |
| 2009/0287274 A1 | 11/2009 | Ridder |
| 2009/0326511 A1 | 12/2009 | Shivkumar |
| 2010/0004704 A1 | 1/2010 | Mazgalev |
| 2010/0010567 A1 | 1/2010 | Deem |
| 2010/0036292 A1 | 2/2010 | Darlington et al. |
| 2010/0042170 A1 | 2/2010 | Caparso |
| 2010/0105993 A1 | 4/2010 | Hassan |
| 2010/0113928 A1 | 5/2010 | Thapliyal |
| 2010/0130836 A1 | 5/2010 | Malchano |
| 2010/0137860 A1 | 6/2010 | Demarais |
| 2010/0137949 A1 | 6/2010 | Mazgalev |
| 2010/0137952 A1 | 6/2010 | Demarais |
| 2010/0145428 A1 | 6/2010 | Cameron |
| 2010/0168624 A1 | 7/2010 | Sliwa |
| 2010/0168731 A1 | 7/2010 | Wu |
| 2010/0168739 A1* | 7/2010 | Wu ................. A61B 18/1492 606/41 |
| 2010/0174282 A1 | 7/2010 | Demarais |
| 2010/0191112 A1 | 7/2010 | Demarais |
| 2010/0204741 A1 | 8/2010 | Tweden |
| 2010/0217162 A1 | 8/2010 | Francischelli |
| 2010/0217369 A1 | 8/2010 | Gross |
| 2010/0222851 A1 | 9/2010 | Deem |
| 2010/0222854 A1 | 9/2010 | Demarais |
| 2010/0234728 A1 | 9/2010 | Foley |
| 2010/0256436 A1 | 10/2010 | Partsch |
| 2010/0268297 A1 | 10/2010 | Neisz |
| 2010/0305392 A1 | 12/2010 | Gross et al. |
| 2011/0009734 A1 | 1/2011 | Foley |
| 2011/0015548 A1 | 1/2011 | Aldrich |
| 2011/0022133 A1 | 1/2011 | Bradford |
| 2011/0040171 A1 | 2/2011 | Foley |
| 2011/0040214 A1 | 2/2011 | Foley |
| 2011/0060324 A1 | 3/2011 | Wu |
| 2011/0092781 A1 | 4/2011 | Gertner |
| 2011/0092880 A1* | 4/2011 | Gertner ................ A61B 5/412 604/20 |
| 2011/0112394 A1 | 5/2011 | Mishelevich |
| 2011/0112400 A1 | 5/2011 | Emery |
| 2011/0118598 A1 | 5/2011 | Gertner |
| 2011/0118600 A1 | 5/2011 | Gertner |
| 2011/0118725 A1 | 5/2011 | Mayse |
| 2011/0137149 A1 | 6/2011 | Gertner |
| 2011/0137298 A1 | 6/2011 | Chen |
| 2011/0172527 A1 | 7/2011 | Gertner |
| 2011/0172528 A1 | 7/2011 | Gertner |
| 2011/0172529 A1 | 7/2011 | Gertner |
| 2011/0178541 A1 | 7/2011 | Azhari |
| 2011/0178570 A1 | 7/2011 | Demarais |
| 2011/0184322 A1 | 7/2011 | Brawer |
| 2011/0184337 A1 | 7/2011 | Evans |
| 2011/0251524 A1 | 10/2011 | Azhari |
| 2011/0257564 A1 | 10/2011 | Demarais et al. |
| 2011/0282203 A1 | 11/2011 | Tsoref |
| 2011/0282249 A1 | 11/2011 | Tsoref |
| 2011/0306851 A1* | 12/2011 | Wang ............................. 600/301 |
| 2012/0089047 A1 | 4/2012 | Ryba et al. |
| 2012/0095371 A1 | 4/2012 | Sverdlik et al. |
| 2012/0130363 A1 | 5/2012 | Kim |
| 2012/0150049 A1* | 6/2012 | Zielinski et al. ............. 600/481 |
| 2012/0197198 A1 | 8/2012 | Demarais |
| 2012/0265198 A1 | 10/2012 | Crow et al. |
| 2012/0265227 A1 | 10/2012 | Sverdlik et al. |
| 2012/0290024 A1* | 11/2012 | Zhang et al. ..................... 607/3 |
| 2012/0296240 A1 | 11/2012 | Azhari |
| 2012/0296329 A1 | 11/2012 | Ng |
| 2013/0012866 A1 | 1/2013 | Deem |
| 2013/0013024 A1 | 1/2013 | Levine |
| 2013/0103028 A1 | 4/2013 | Tsoref |
| 2013/0165926 A1 | 6/2013 | Mathur et al. |
| 2013/0204242 A1 | 8/2013 | Sverdlik et al. |
| 2013/0211396 A1 | 8/2013 | Sverdlik et al. |
| 2013/0211437 A1 | 8/2013 | Sverdlik et al. |
| 2013/0218054 A1 | 8/2013 | Sverdlik et al. |
| 2013/0218068 A1 | 8/2013 | Sverdlik et al. |
| 2013/0274735 A1 | 10/2013 | Hastings et al. |
| 2013/0331813 A1 | 12/2013 | Barbut et al. |
| 2014/0012133 A1 | 1/2014 | Sverdlik et al. |
| 2014/0194866 A1 | 7/2014 | Wang |
| 2014/0213873 A1 | 7/2014 | Wang |
| 2014/0221805 A1 | 8/2014 | Wang |
| 2014/0276742 A1 | 9/2014 | Nabutovsky et al. |
| 2015/0011843 A1 | 1/2015 | Toth et al. |
| 2015/0073400 A1 | 3/2015 | Sverdlik et al. |
| 2015/0164401 A1 | 6/2015 | Toth et al. |
| 2015/0173673 A1 | 6/2015 | Toth et al. |
| 2015/0216590 A1 | 8/2015 | Wang et al. |
| 2015/0224326 A1 | 8/2015 | Toth et al. |
| 2015/0289929 A1 | 10/2015 | Toth et al. |
| 2015/0297139 A1 | 10/2015 | Toth |
| 2016/0113699 A1 | 4/2016 | Sverdlik et al. |

FOREIGN PATENT DOCUMENTS

| | | |
|---|---|---|
| EP | 2460486 | 6/2012 |
| EP | 2460486 A1 | 6/2012 |
| WO | 99/40957 | 8/1999 |
| WO | 03/097162 | 11/2003 |
| WO | 2006/072928 | 7/2006 |
| WO | 2007/134258 | 11/2007 |
| WO | 2010/067360 | 6/2010 |
| WO | 2011/024159 | 3/2011 |
| WO | 2011/141918 | 11/2011 |
| WO | 2012/120495 | 9/2012 |
| WO | 2012/122157 | 9/2012 |
| WO | 2013-030743 | 3/2013 |
| WO | 2013030738 | 3/2013 |
| WO | WO2013049601 | 4/2013 |
| WO | 2013/111136 | 8/2013 |
| WO | 2013/121424 | 8/2013 |
| WO | 2013/157009 | 10/2013 |
| WO | 2014-029355 | 2/2014 |
| WO | 2014/029355 A1 | 2/2014 |
| WO | 2014/071223 A1 | 5/2014 |
| WO | 2014/160832 A2 | 10/2014 |
| WO | 2015/057696 A1 | 4/2015 |

OTHER PUBLICATIONS

Cassak D, "Endosense: Facing technology and financing challenges in AF," In-Vivo: The Business & Medicine Report, 36-44, Mar. 2010.

Di Biase L et al., "Prevention of phrenic nerve injury during epicardial ablation: Comparison of methods for separating the phrenic nerve from the epicardial surface," Heart Rhythm 2009;6:957-961.

(56) References Cited

OTHER PUBLICATIONS

Matsuo S et al., "Novel technique to prevent left phrenic nerve injury during epicardial catheter ablation," Circulation 2008;117:e471.

Nakahara S et al., "Intrapericardial balloon placement for prevention of collateral injury during catheter ablation of the left atrium in a porcine model," Heart Rhythm 2010;7:81-87.

Shen J et al., "The surgical treatment of atrial fibrillation Heart Rhythm," vol. 6, No. 8S, August Supplement 2009.

Sacher F et al., "Phrenic Nerve Injury After Catheter Ablation of Atrial Fibrillation," Indian Pacing Electrophysiol J. Jan.-Mar. 2007; 7(1): 1-6.

A Restriction Requirement dated Feb. 25, 2013, which issued during the prosecution of U.S. Appl. No. 12/780,240.

Tanaka S et al., "Development of a new vascular endoscopic system for observing inner wall of aorta using intermittent saline jet" World Congress on Medical Physics and Biomedical Engineering, Sep. 7-12, 2009, Munich, Germany.

Tearney GJ et al., "Three-Dimensional coronary artery microscopy by intracoronary optical frequency domain imaging" JACC Cardiovasc Imaging. Nov. 2008; 1(6): 752-761.

William E. Cohn, et al., "Contrast pericardiography facilitates intrapericardial navigation under fluoroscopy", Ann Thorac Surg 2010; 90: 1537-40. Accepted for publication Jun. 7, 2010.

Srijoy Mahapatra, et al., "Pressure frequency characteristics of the pericardial space and thorax during subxiphoid access for epicardial ventricular tachycardia ablation", Heart Rhythm 2010; 7:604-609.

Schuessler RB et al., "Animal studies of epicardial atrial ablation," Heart Rhythm, vol. 6, No. 12S, S41-S45, December Supplement 2009.

An International Search Report and a Written Opinion both dated Oct. 26, 2011, which issued during the prosecution of Applicant's PCT/IL11/00382.

An International Search Report and a Written Opinion both dated Sep. 17, 2012, which issued during the prosecution of Applicant's PCT/IL2012/000100.

An International Preliminary Report on Patentability dated Nov. 20, 2012, which issued during the prosecution of Applicant's PCT/IL11/00382.

An International Search Report dated Jul. 31, 2008, which issued during the prosecution of Applicant's PCT/US07/68818.

An Office Action dated Dec. 20, 2012, which issued during the prosecution of U.S. Appl. No. 11/653,115.

An Office Action dated Feb. 19, 2013, which issued during the prosecution of U.S. Appl. No. 13/010,555.

Fajardo et al., Effects of Hyperthermia in a Malignant Tumor, Cancer 45:613-623 (1980).

Short et al., Physical Hyperthermia and Cancer Therapy, Proceedings of the IEEE 68:133-142 (1980) p. 136, col. 2, para 6.

U.S. Appl. No. 60/370,190, filed Apr. 8, 2002.

U.S. Appl. No. 60/307,124, filed Jul. 23, 2001.

An Office Action dated May 17, 2013, which issued during the prosecution of U.S. Appl. No. 12/780,240.

An Invitation to pay additional fees dated Jun. 7, 2013, which issued during the prosecution of Applicant's PCT/IL2013/050134.

An International Search Report and a Written Opinion both dated Aug. 12, 2013 which issued during the prosecution of Applicant's PCT/IL2013/050134.

An International Search Report and a Written Opinion both dated Feb. 18, 2011 which issued during the prosecution of Applicant's PCT/IL2010/000683.

An International Preliminary Report of patentability dated Feb. 28, 2012 which issued during the prosecution of Applicant's PCT/IL2010/000683.

F. Mahfoud et al., Catheter-Based renal denervation increases insulin sensitivity and improves glucose metabolism. European Heart Journal 2010.

F. Mahfoud et al., Effects of Renal Sympathetic Denervation on Glucose Metabolism in Patients with Resistant Hypertension: A Pilot Study. Circulation 2011: 123 1940-1946.

Tai et al., Analysis of Nerve Conduction Including by Direct Current, J Comput Neuro. Published Online on 2009.

Ariav et al., Electrical Stimulation Induced Relaxation of Isolated Pig Aortas, Scientific Sessions 2011. American Heart Association. Abstract.

Stella et al., Cardiovascular Effects of Efferent renal nerve stimulation, Clin and Exper. Theory and Practice, 97-111, 1987.

Mortimer and Bhadra., Peripheral Nerve and Muscle Stimulation, Chapter 4.2, 1-48, 2004.

Stella et al., Effects of afferent renal nerve stimulation on renal hemodynamic and excretory functions, American Journal of physiology, 576-583, 1984.

Renal Sympathetic denervation in patients with treatment resistant hypertension, (1-7) Published online Nov. 2010.

Zhang et al., Mechanism of Nerve conduction Block induced by High-Frequency Biphasic Electrical Currents, IEEE Biomedical Engineering vol. 53 No. 12, 2006.

Bhadra et al., Reduction of the Onset Response in High-Frequency Nerve Block with Amplitude Ramps from Non-Zero Amplitudes, 650-653, 2009 IEEE.

Tai et al., Stimulation of Nerve Block by High-Frequency Sinusoidal Electrical Current Based on the Hodgkin-Huxley Model, IEEE Neural Systems and Rehabilitation engineering, vol. 13 No. 3, 2005.

Tsui, Electrical Nerve Stimulation, Springer Atlas of Ultrasound, pp. 9-18, 2008.

Bartus et al., Denervation (ablation) of Nerve Terminalis in renal arteries: early results of interventional treatment of arterial hypertension in Poland, Kardiologia Polska 2013, 71, 2: 152-158.

Krum et al., Catheter-Based Renal sympathetic denervation for resistant hypertension: A multicentre safety and proof-of-principle cohort study, Lancet 2009.

Chinushi M. et al., Blood pressure and autonomic responses to electrical stimulation of the renal arterial nerve before and after ablation of the renal artery, Pubmed, Hyper tension, Feb. 2013 61;(2) 450-6.

Wojakowski and Tendera, Renal sympathetic nerve in pathophysiology of resistant hypertension, European Society of Cardiology, downloaded on Jun. 2013.

Chinushi et al., Hemodynamic Responses and Histological Effects of Radiofrequency catheter Ablation to renal artery Sympathetic nerve. Abstract, downloaded on Jun. 2013.

Berjano, Biomedical Engineering Online Theoretical modeling for Radiofrequency Ablation: state-of-the-art and challenges for the future, published Apr. 2006.

Young and Henneman, Reversible block of nerve Conduction by Ultrasound, Archive of Neurology vol. 4, 1961.

Ballantine et al., Focal Destruction of nervous tissue by focused ultrasound : Biophysical factors influencing its Application, Medical Acoustics Research Group, 1956.

Colucci et al., Focused Ultrasound effects on nerve action potential in vitro, Department of Radiology, Harvard Medical Scholl, Ultrasound Med Biolog. 2009, 35(10); 1773-174.

Damianou, MRI Monitoring of the effects of tissue interfaces in the penetration of high intensity focused ultrasound in kidney in vivo, Ultrasound in Med & Bilo., vol. 30 No. 9, 2004.

Daum et al., In vivo Demonstration of noninvasive thermal surgery of the liver and kidney using an ultrasonic phase array, Ultrasound in Med & Bilo., vol. 25 No. 7, 1087-1098, 1999.

Foley et al., Image guided HIFU Neurolysis of peripheral nerve to treat Spasticity and Pain, Ultrasound in Med & Bilo., vol. 30 No. 9, 1199-1207, 2004.

Foley et al., Image guided High-Intensity focused Ultrasound for Condition block of peripheral nerves, Biomed Engineering, vol. 35 No. 1, 2007.

Zhang and Solomon, Nerve Ablation by high Intensity focused Ultrasound (HIFU) in swine model: Investigating HIFU as a non invasive Nerve block tool, WCIO 2011. Abstract.

Hynynen et al., Noninvasive arterial occlusion using MRI-Guided focused Ultrasound, Ultrasound in Med & Bilo., vol. 22 No. 8, 1071-1077, 1996.

Iwamoto et al., Focused Ultrasound for Tactile Felling display, ICAT 2001.

(56) References Cited

OTHER PUBLICATIONS

Lele, Effects of Ultrasonic radiation on peripheral Nerve, with Observation on local Hearting, Experimental Neurology 8, 47-83, 1963.
Miharn et al., Temporally-Specific modification of Myelinated Axon excitability in vitro following a single ultrasound pulse, Ultrasound in Med & Bilo., 1990.
Rubin et al., Acute effects of Ultrasound on skeletal muscle oxygen tension , blood flow and capillary density, Ultrasound in Med & Bilo., vol. 16 No. 3, 271-277, 1990.
Renal sympathetic nerve ablation for Uncontrolled Hypertension, The New England journal of medicine, 932-934, 2009.
Wu et al., Preliminary Experience using high Intensity focused Ultrasound for the treatment of patient with advanced stage renal malignancy. The Journal of Urology, vol. 170, 2237-2240, 2003.
Young and Henneman, Functional Effects of focused Ultrasound on Mammalian nerves, Science New Series, vol. 134, No. 3489, 1961, 1521-1522.
Mizelle et al., Role of Renal nerve in Compensatory adaptation to chronic reduction in sodium intake, American Physiological Society, 1987.
Gibson, The Present Status of Renal Sympathectomy, California and Western Medicine, vol. 45, No. 1, 1936.
Kassab et al., Renal Denervation Attenuates the Sodium Retention and Hypertension Associated With Obesity, Hypertension, 1997. Abstract.
Winternitz et al., Role of the Renal Sympathetic Nerves in the Development and Maintenance of Hypertension in the Spontaneously Hypertensive Rat, J. Clin Invest 66(5), 1980. Abstract.
Augustyniak et al., Sympathetic overactivity as a cause of hypertension in chronic renal failure, Hypertension vol. 20, Issue 1, 2002. Abstract.
Fletcher, Effect of episodic hypoxia on sympathetic activity and blood pressure, Respiration Physiology, vol. 119, issue 2-3, 2000. Abstract.
Fletcher et al., Blood pressure response to chronic episodic hypoxia: the renin-angiotensin system, Journal of Applied physiology, 2001.
Illis, Spinal Cord Synapses in the Cat: The Reaction of the Boutons Termineaux at the Motoneurone Surface to Experimental Denervation, Brain a Journal of Neurology, vol. 87 issue 3, 1963, First page only.
Kopelman et al., Upper dorsal thoracoscopic sympathectomy for palmar hyperhidrosis. The use of harmonic scalpel versus diathermy. Ann Chir Gynaecol. 2001;90(3):203-5. Abstract.
Hashmonai et al., Thoracoscopic sympathectomy for palmar hyperhidrosis, Surgical Endoscopy May 2001, vol. 15, Issue 5, pp. 435-441.
Yoshimoto et al., Relationship between renal sympathetic nerve activity and renal blood flow during natural behavior in rats, American Journal of Physiology vol. 286, 2004.
DiBona. Dynamic Analysis of patterns of renal sympathetic nerve activity: Implications of renal functions, Exp Physiol. 90.2 pp. 159-161, 2004.
Valente et al., Laparoscopic renal denervation for intractable ADPKD-related pain, Nephrology Dialysis Transplantation vol. 6 issue 1, 2000.
International Search report dated Aug. 11, 2015, which issued for application PCT/IB2015/053350.
Lu (2015) Selective Proximal Renal Denervation Guided by Autonomic Responses Evoked via High-Frequency Stimulation in a Preclinical Canine Model.
Changfeng (2009) Analysis of nerve conduction block induced by direct current.
Tsui (2008) Chapter 2 of Atlas of ultrasound and nerve stimulation guided regional anesthesia.
Stella (1987) Cardiovascular effects of afferent renal nerve stimulation.
Changfeng (2005) Simulation of nerve block by high frequency sunusoidal electrical current.
Mortimer (2004) Peripheral nerve and muscle stimulation (Chapter 4.2 in 'Neuroprosthetics theory and practice', p. 638-632).
Mahfoud (2011) Renal sympathetic denervation on glucose metabolism in patients with resistant hypertension.
Esler (2010) Renal sympathetic denervation in patients with treatment-resistant hypertension (The Symplicity HTN-2 Trial).
Schwarz et al;(2015) Autonomix presentation at TCT—Guidewire-Based Autonomic Neural Sensing From the Artery Lumen.
International Search Report and Written Opinion dated Aug. 11, 2015 from the International Searching Authority in counterpart International Application No. PCT/IB2015/053350.
Pokushalov, Evgeny, et al. "A randomized comparison of pulmonary vein isolation with versus without concomitant renal artery denervation in patients with refractory symptomatic atrial fibrillation and resistant hypertension." Journal of the American College of Cardiology 60.13 (2012): 1163-1170.
An English translation of an Office Action dated Nov. 18, 2016, which issued during the prosecution of Chinese Patent Application No. 201380069261.2.
Extended European Search Report dated Jun. 16, 2016 in European Patent Application No. 13850508.6.
Kilgore, Kevin L., et al. "Combined direct current and high frequency nerve block for elimination of the onset response." Engineering in Medicine and Biology Society, 2009. EMBC 2009. Annual International Conference of the IEEE. IEEE, 2009.
Krum, H., et al. "Device-based antihypertensive therapy: therapeutic modulation of the autonomic nervous system." Circulation 123.2 (2011): 209.
Sarafidis PA, Bakris GL. Resistant hypertension: An overview of evaluation and treatment. J Am Coll Cardiol. 2008;52:1749-1757.
Calhoun DA, Jones D, Textor S, Goff DC, Murphy TP, Toto RD, White A, Cushman WC, White W, Sica D, Ferdinand K, Giles TD, Falkner B, Carey RM. Resistant hypertension: Diagnosis, evaluation, and treatment: A scientific statement from the American Heart Association professional education committee of the council for high blood pressure research. Circulation. 2008;117:e510-526.
Schlaich MP, Sobotka PA, Krum H, Whitbourn R, Walton A, Esler MD. Renal denervation as a therapeutic approach for hypertension: Novel implications for an old concept. Hypertension. 2009;54:1195-1201.
Esler MD, Bohm M, Sievert H, Rump CL, Schmieder RE, Krum H, Mahfoud F, Schlaich MP. Catheter-based renal denervation for treatment of patients with treatment-resistant hypertension: 36 month results from the Symplicity htn-2 randomized clinical trial. Eur Heart J. 2014;35:1752-1759.
Mahfoud F, Cremers B, Janker J, Link B, Vonend O, Ukena C, Linz D, Schmieder R, Rump LC, Kindermann I, Sobotka PA, Krum H, Scheller B, Schlaich M, Laufs U, Bohm M. Renal hemodynamics and renal function after catheter-based renal sympathetic denervation in patients with resistant hypertension. Hypertension. 2012;60:419-424.
Krum H, Schlaich M, Whitbourn R, Sobotka PA, Sadowski J, Bartus K, Kapelak B, Walton A, Sievert H, Thambar S, Abraham WT, Esler M. Catheter-based renal sympathetic denervation for resistant hypertension: A multicentre safety and proof-of-principle cohort study. Lancet. 2009;373:1275-1281.
Krum H, Schlaich MP, Sobotka PA, Bohm M, Mahfoud F, Rocha-Singh K, Katholi R, Esler MD. Percutaneous renal denervation in patients with treatment-resistant hypertension: Final 3-year report of the symplicity htn-1 study. Lancet. 2014;383:622-629.
Esler MD, Krum H, Sobotka PA, Schlaich MP, Schmieder RE, Bohm M. Renal sympathetic denervation in patients with treatment-resistant hypertension (the symplicity htn-2 trial): A randomised controlled trial. Lancet. 2010;376:1903-1909.
Kandzari DE, Bhatt DL, Sobotka PA, O'Neill WW, Esler M, Flack JM, Katzen BT, Leon MB, Massaro JM, Negoita M, Oparil S, Rocha-Singh K, Straley C, Townsend RR, Bakris G. Catheter-based renal denervation for resistant hypertension: Rationale and design of the symplicity htn-3 trial. Clin Cardiol. 2012;35:528-535.
Ruilope LM, Arribas F. Resistant hypertension and renal denervation. Considerations on the results of the symplicity htn-3 trial. Rev Esp Cardiol (Engl Ed). 2014.

(56) References Cited

OTHER PUBLICATIONS

Kjeldsen SE, Fadl Elmula FE, Persu A, Jin Y, Staessen JA. Renal sympathetic denervation in the aftermath of symplicity htn-Blood Press. 2014;23:256-261.
Ruilope LM. Was there real denervation in the symplicity htn-3 trial? Eur Heart J. 2014;35:1699-1700.
Bohm M, Mahfoud F. Symplicity htn-3 trial: What is it and what does it mean? Eur Heart J. 2014;35:1697-1698.
Esler M. Illusions of truths in the symplicity htn-3 trial: Generic design strengths but neuroscience failings. J Am Soc Hypertens. 2014;8:593-598.
Warchol-Celinska E, Januszewicz A, Prejbisz A, Kadziela J. Renal denervation after the symplicity htn-3 trial. Postepy Kardiol Interwencyjnej. 2014;10:75-77.
Patel HC, Hayward C, Di Mario C. Symplicity htn 3: The death knell for renal denervation in hypertension? Glob Cardiol Sci Pract. 2014;2014:94-98.
Papademetriou V, Tsioufis C, Doumas M. Renal denervation and symplicity htn-3: "Dubium sapientiae initium" (doubt is the beginning of wisdom). Circ Res. 2014;115:211-214.
Bohm M. [interview with prof. Dr. Med. Michael bohm: Lessons from symplicity htn—"Denervation only within the scope of studies or registries" (interview by dr. Med. Dirk einecke)]. MMW Fortschr Med. 2014;156:19-20.
Persu A, Jin Y, Fadl Elmula FE, Jacobs L, Renkin J, Kjeldsen S. Renal denervation after symplicity htn-3: An update. Curr Hypertens Rep. 2014;16:460.
Schmieder RE. Hypertension: How should data from symplicity htn-3 be interpreted? Nat Rev Cardiol. 2014;11:375-376.
Pathak A, Ewen S, Fajadet J, Honton B, Mahfoud F, Marco J, Schlaich M, Schmieder R, Tsioufis K, Ukena C, Zeller T. From symplicity htn-3 to the renal denervation global registry: Where do we stand and where should we go? EuroIntervention. 2014;10:21-23.
Luscher TF, Mahfoud F. Renal nerve ablation after symplicity htn-3: Confused at the higher level? Eur Heart J. 2014;35:1706-1711.
"Blood pressure response to renal nerve stimulation in patients undergoing renal denervation: a feasibility study", Gal et al., Journal of Human Hypertension (2014), 1-4, Macmillan Publishers Limited.
International Search Report and Written Opinion, dated Apr. 17, 2014, which issued in PCT/IL2013/050903.
Chinushi et al., 'Blood Pressure and Autonomic Responses to Electrical Stimulation of the Renal Arterial Nerves Before and After Ablation of the Renal Artery' Hypertension 2013;61:450-456.
pcta.org, 'New Medtronic Multi-Electrode Renal Denervation Device Gets CE Mark and Australian Aproval' (Dec. 6, 2013) http://www.ptca.org/news/2013/1206_MEDTRONIC_SYMPLICITY.html.
BusinessWire, 'St. Jude Medical Receives European Approval for New Renal Denervation System That Reduces Total Ablation Time by More Than 80 Percent' (Aug. 29, 2013) 2013 European Society of Cardiology.
mananatomy.com, 'Duodenum' http://www.mananatomy.com/digestive-system/duodenum.
Rosas-Ballina et al., 'Splenic nerve is required for cholinergic antiinflammatory pathway control of TNF in endotoxemia' Aug. 5, 2008, vol. 105, No. 31 www.pnas.org/cgi/doi/10.1073/pnas.0803237105.
Straub et al., 'A bacteria-induced switch of sympathetic effector mechanisms augments local inhibition of TNF-á and IL-6 secretion in the spleen' Jul. 2000 The FASEB Journal vol. 14 No. 10 1380-1388.
Gestel et al., 'Autonomic dysfunction in patients with chronic obstructive pulmonary disease (COPD)' J Thorac Dis 2010; 2: 215-222.
Hering et al., 'Renal Denervation in Moderate to Severe CKD' J Am Soc Nephrol. [Jul. 2012]; 23(7): 1250-1257.
Jonson et al., 'Afferent electrical stimulation of mesenteric nerves inhibits duodenal HCO3 secretion via a spinal reflex activation of the splanchnic nerves in the rat' [1988] Acta Physiologica Scandinavica, 133: 545-550. doi: 10.1111/j. 1748-1716.1988. tb08439.x.
Jonson et al., 'Splanchnic nerve stimulation inhibits duodenal HCO3-secretion in the rat' Am J Physiol. [Dec. 1988];255 (6 Pt 1):G709-12.
Kees et al., 'Via beta-adrenoceptors, stimulation of extrasplenic sympathetic nerve fibers inhibits lipopolysaccharide-induced TNF secretion in perfused rat spleen' J Neuroimmunol. Dec. 2003;145(1-2):77-85.

\* cited by examiner

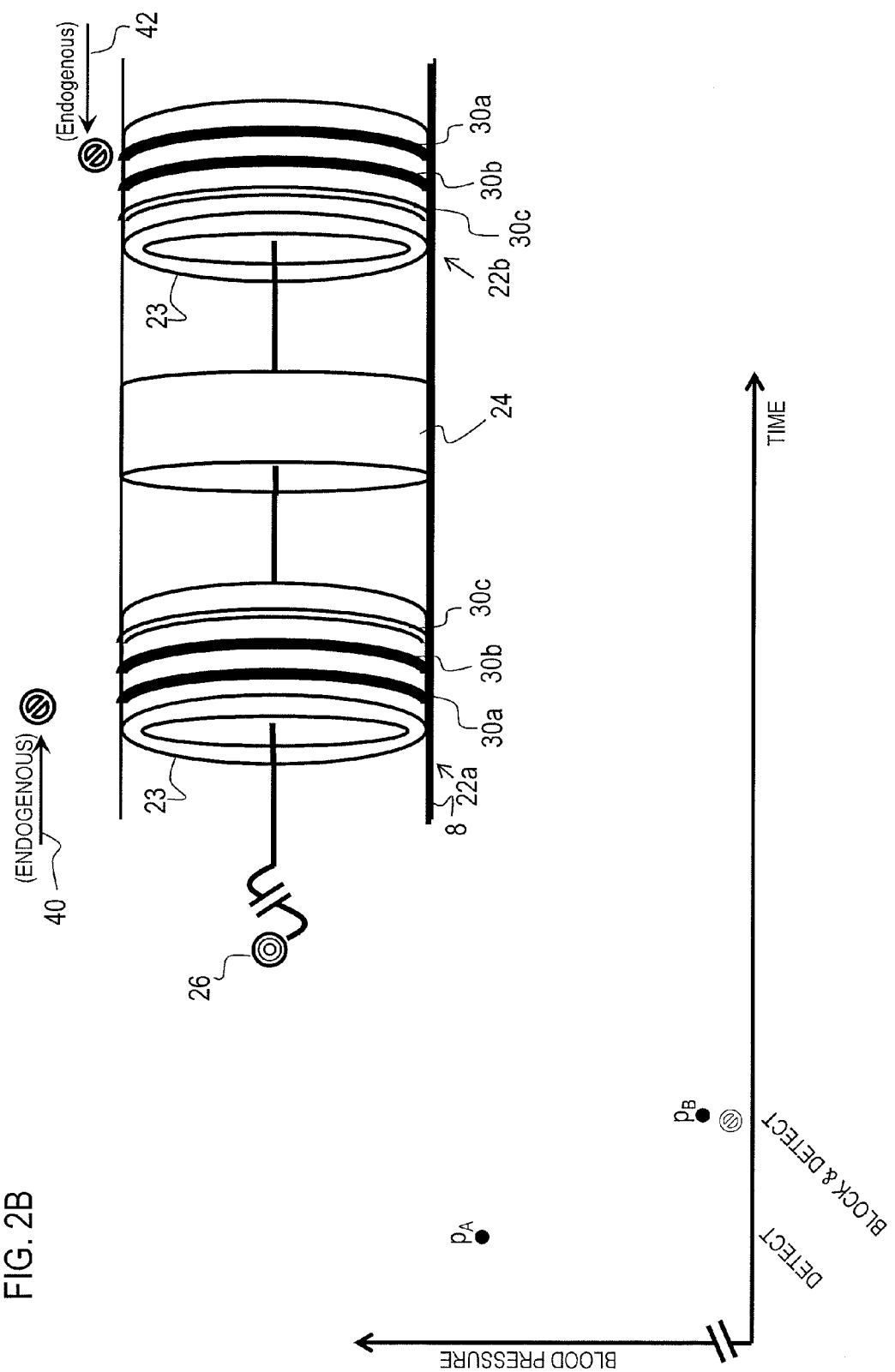

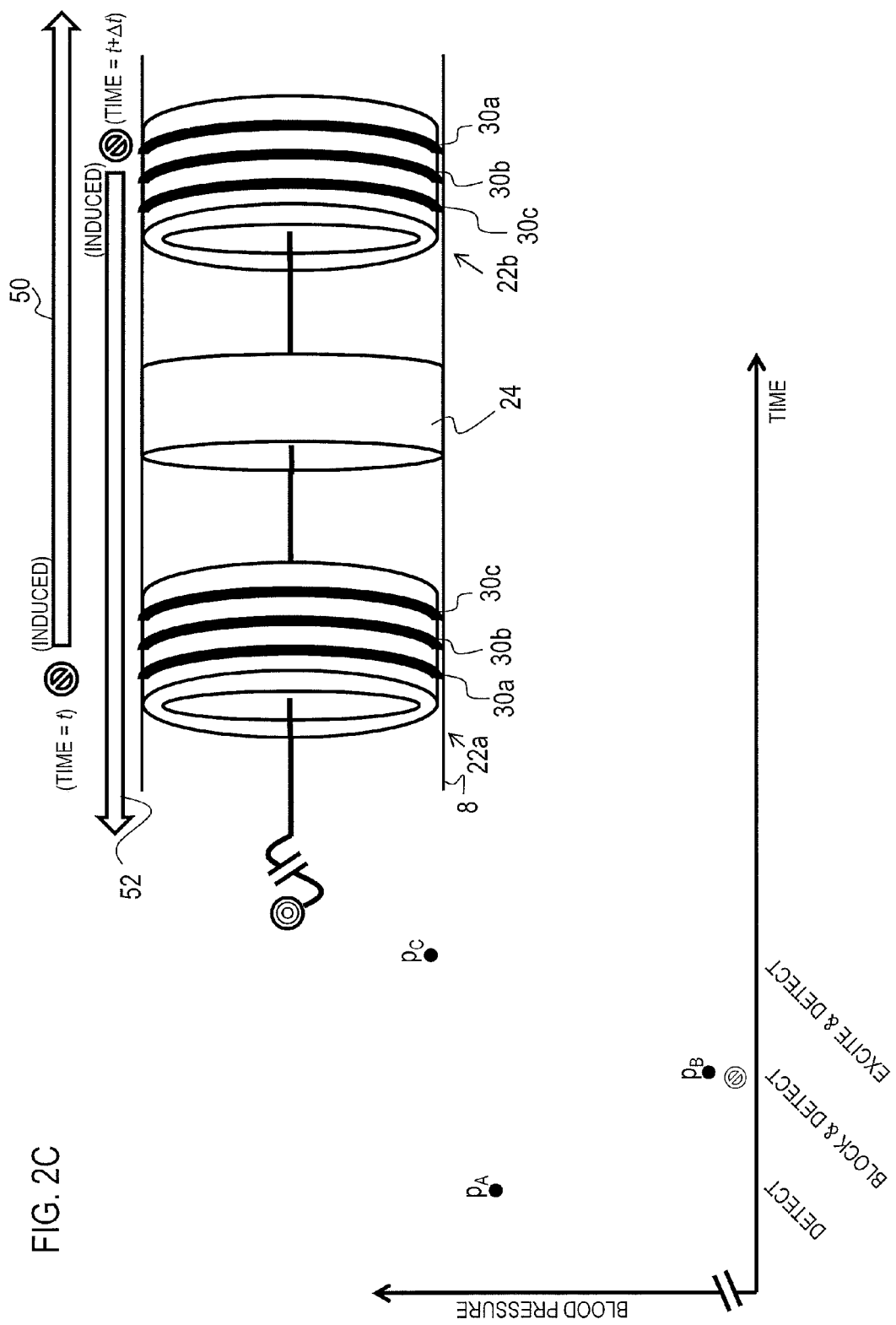

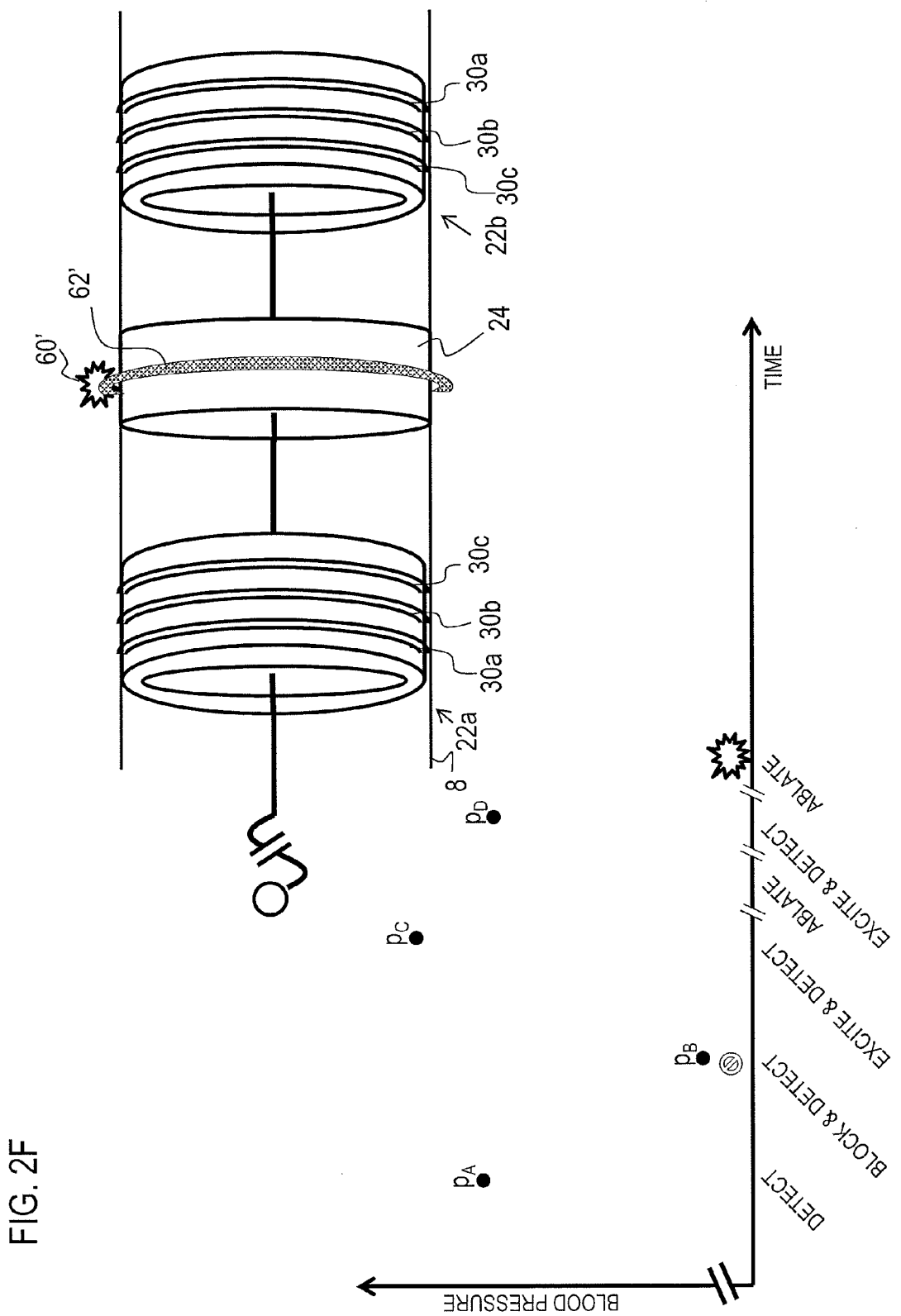

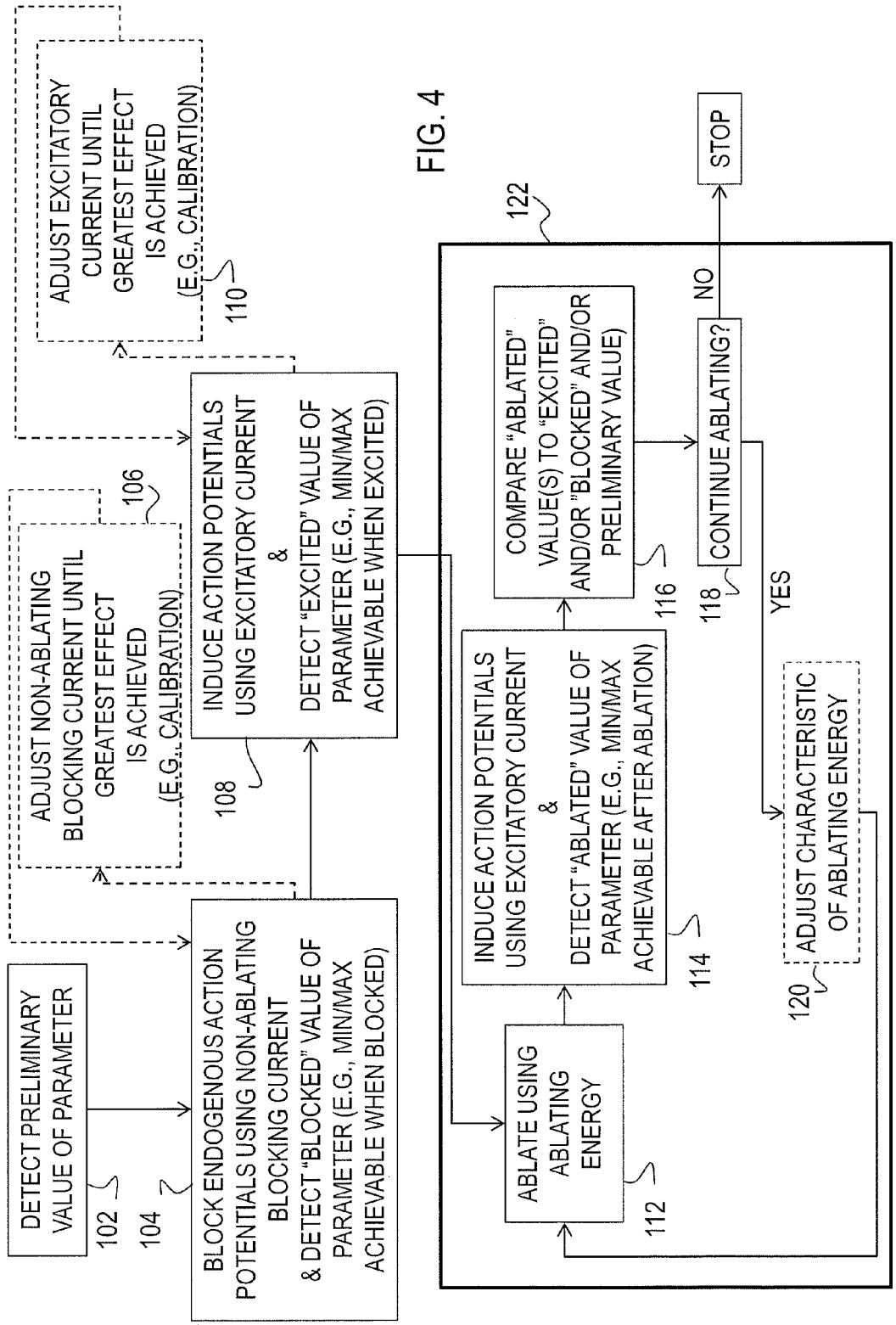

PATIENT SELECTION USING A TRANSLUMINALLY-APPLIED ELECTRIC CURRENT

CROSS-REFERENCES TO RELATED APPLICATIONS

The present application claims priority from U.S. Provisional Patent Application 61/722,293 to Gross, filed Nov. 5, 2012.

FIELD OF THE INVENTION

Applications of the present invention relate generally to ablation of tissue. Some applications of the present invention relate more specifically to ablation of tissue of the renal artery.

BACKGROUND

Hypertension is a prevalent condition in the general population, particularly in older individuals. Sympathetic nervous pathways, such as those involving the renal nerve, are known to play a role in regulating blood pressure. Ablation of renal nerve tissue from the renal artery is a known technique for treating hypertension.

SUMMARY OF THE INVENTION

Some applications of the invention comprise detecting one or more values indicative of blood pressure of the subject while blocking endogenous action potentials and/or initiating induced action potentials in the renal nerve of the subject. Based on these one or more values, the potential benefit of a first and/or a successive application of ablative energy to the renal nerve may be predicted. For some applications of the invention, a control unit controls the blocking, initiating, and ablating, and automatically applies (or automatically does not apply) the first and/or successive application of ablative energy.

There is therefore provided, in accordance with an application of the present invention, apparatus for facilitating ablation of nerve tissue of a subject, the apparatus including:

an ablation unit, configured to be percutaneously advanced to a site adjacent to a first portion of the nerve tissue of the subject;

at least one electrode unit, coupled to the ablation unit, and configured to be percutaneously advanced to a site adjacent to a second portion of the nerve tissue of the subject, and to initiate unidirectional action potentials in the nerve tissue, such that the unidirectional action potentials propagate toward the first portion of the nerve tissue; and a control unit, configured:
to drive the ablation unit to ablate, at least in part, the first portion of the nerve tissue of the subject, and
to drive the at least one electrode unit to initiate the unidirectional action potentials by applying an excitatory current to the second portion of the nerve tissue.

In an application, the at least one electrode unit includes a first electrode unit and a second electrode unit, the first electrode unit being coupled to the ablation unit on a first side of the ablation unit, and the second electrode unit being coupled to the ablation unit on a second side of the ablation unit, each electrode unit being configured to initiate unidirectional action potentials in the nerve tissue, such that the action potentials propagate toward the first portion of the nerve tissue.

In an application, the ablation unit includes a radio-frequency ablation unit, and the control unit is configured to drive the radio-frequency ablation unit to ablate the first portion of the nerve tissue by applying an ablative radio-frequency current to the first portion of the nerve tissue.

In an application, the ablation unit includes an ultrasound ablation unit, and the control unit is configured to drive the ultrasound ablation unit to ablate the first portion of the nerve tissue by applying ablative ultrasound energy to the first portion of the nerve tissue.

In an application, the electrode unit is configured to apply a non-ablative blocking current to the second portion of the nerve tissue of the subject, the non-ablative blocking current being configured to reversibly block endogenous action potentials from propagating through the second portion of the nerve tissue, and the control unit is configured to drive the at least one electrode unit to apply the non-ablative blocking current.

In an application, the nerve tissue includes nerve tissue of a blood vessel of the subject, and at least the ablation unit is configured to be transluminally delivered to the blood vessel of the subject.

In an application, the electrode unit is configured to be transluminally delivered to the blood vessel of the subject.

In an application, the blood vessel includes a renal artery of the subject, and at least the ablation unit is configured to be transluminally delivered to the renal artery of the subject.

In an application, the apparatus further includes a longitudinal member, having a distal portion that is configured to be percutaneously advanced toward the nerve tissue of the subject, and the ablation unit and the electrode unit are coupled to the longitudinal member.

In an application, the distal portion of the longitudinal member is bifurcated so as to have two distal portions, each distal portion being configured to be transluminally advanced into a respective renal artery of the subject.

In an application, the apparatus further includes a sensor, configured to detect a physiological response of the subject to the unidirectional action potentials initiated by the electrode unit.

In an application, the apparatus further includes a longitudinal member, configured to be percutaneously advanced toward the nerve tissue of the subject, and the ablation unit, the electrode unit, and the sensor are coupled to the longitudinal member.

In an application, the sensor is configured to be disposed in an aorta of the subject.

In an application, the sensor includes a blood pressure sensor.

In an application, the control unit is configured to receive information indicative of the detected physiological response, and to drive the ablation unit at least in part responsively to the information indicative of the detected physiological response.

In an application, the control unit is configured:
to drive, during a first period, the at least one electrode unit to apply a non-ablative blocking current to the second portion of the nerve tissue of the subject, the blocking current being configured to temporarily block endogenous action potentials from propagating through the second portion of the nerve tissue,
to receive a first value of a factor indicative of the response, the first value being detected after a start of the application of the non-ablative blocking current, and
to drive the ablation unit at least in part responsively to the received first value.

In an application, the control unit is configured:

to drive, during a second period, the at least one electrode unit to apply the excitatory current, to receive a second value of the factor, the second value being detected after a start of the application of the excitatory current, and to drive the ablation unit at least in part responsively to the received second value.

In an application, the sensor is configured to detect the first value of the factor after the start of the application of the non-ablative blocking current, and to provide the first value of the factor to the control unit.

There is further provided, in accordance with an application of the present invention, apparatus for facilitating ablation of nerve tissue of a subject, the nerve tissue conducting endogenous action potentials to an anatomical structure of the subject, the structure being capable of altering a parameter of the subject at least in part responsively to the endogenous action potentials, the apparatus including:

a sensor, configured to detect a factor indicative of the parameter of the subject;

an ablation unit, configured to be percutaneously advanced to a site adjacent to a first portion of the nerve tissue of the subject;

at least one electrode unit, configured to be percutaneously advanced to a site adjacent to a second portion of the nerve tissue of the subject; and a control unit, configured to:

drive the electrode unit to initiate induced action potentials in the second portion of the nerve tissue of the subject by applying an excitatory current to the second portion of the nerve tissue, the action potentials inducing the structure to alter the parameter of the subject, receive, from the sensor, information indicative of the factor, and at least in part responsively to the information, drive the ablation unit to apply ablative energy to the first portion of the tissue.

In an application, the electrode unit is configured to be positioned with respect to the ablation unit such that the induced action potentials propagate toward the first portion of the nerve of the subject.

In an application, the control unit is further configured to drive the electrode unit to apply a non-ablative blocking current to the second portion of the nerve.

There is further provided, in accordance with an application of the present invention, a method for ablating nerve tissue of a renal artery of a subject, the method including:

applying a non-ablative electrical current to the nerve tissue;

subsequently applying a first application of ablative energy to the nerve tissue;

receiving (1) a first value of the subject, the first value being indicative of a blood pressure of the subject after a start of the application of the non-ablative electrical current and before the first application of the ablative energy, and (2) a second value of the subject, the second value being indicative of the blood pressure of the subject after the first application of the ablative energy; and at least in part responsively to a difference between the first value and the second value, applying a second application of the ablative energy to the nerve tissue.

In an application, applying the second application of the ablative energy includes applying a second application of ablative energy that has an intensity that is greater than an intensity of the first application of the ablative energy.

In an application, receiving the first value includes receiving a first value that is indicative of a blood pressure of the subject after an end of the application of the non-ablative electrical current.

In an application, the method further includes receiving a preliminary value indicative of the parameter of the subject before the application of the non-ablative electrical current, and applying the ablative energy includes applying the ablative energy at least in part responsively to (1) the difference between the first value and the second value, and (2) the preliminary value.

In an application, receiving the first value indicative of the parameter of the subject after the start of the application of the non-ablative electrical current includes receiving the first value indicative of the parameter of the subject during the application of the non-ablative electrical current.

In an application, receiving the first value indicative of the parameter of the subject after the start of the application of the non-ablative electrical current includes receiving the first value indicative of the parameter of the subject after the application of the non-ablative electrical current.

In an application, the non-ablative electrical current includes an excitatory current, and applying the non-ablative electrical current includes initiating action potentials in the first portion of the nerve tissue using the excitatory current.

In an application, the non-ablative electrical current includes a blocking current, and applying the non-ablative electrical current includes blocking action potentials in the first portion of the nerve tissue using the blocking current.

There is further provided, in accordance with an application of the present invention, a method for use with nerve tissue of a subject, the nerve tissue conducting endogenous action potentials to an anatomical structure of the subject, the structure being capable of altering a parameter of the subject at least in part responsively to the endogenous action potentials, the method including:

during a first period, blocking the endogenous action potentials from propagating through the nerve tissue by applying a non-ablative blocking current to the nerve tissue and, after the start of the application of the non-ablative blocking current, detecting a first value of a factor indicative of the parameter of the subject; and during a second period, initiating unidirectional action potentials in the nerve tissue by applying an excitatory current to the nerve tissue and, after the start of the application of the excitatory current, detecting a second value of the factor indicative of the parameter of the subject.

In an application, the method further includes, during a third period, detecting a third value of the factor indicative of the parameter of the subject in the absence of the non-ablative blocking current and the excitatory current.

In an application, the method further includes, responsively to the first and second values, determining a sensitivity of the parameter to action potentials in the nerve tissue.

In an application, the method further includes, responsively to the first and second values, selecting the subject for a treatment including ablation of the nerve tissue.

In an application, detecting the first value after the start of the application of the non-ablative blocking current includes detecting the first value during the application of the non-ablative blocking current.

In an application, detecting the first value after the start of the application of the non-ablative blocking current includes detecting the first value after the application of the non-ablative blocking current.

In an application, detecting the second value after the start of the application of the excitatory current includes detecting the second value during the application of the excitatory current.

In an application, detecting the second value after the start of the application of the excitatory current includes detecting the second value after the application of the excitatory current.

In an application, the nerve tissue includes nerve tissue of a blood vessel of a subject, and blocking and initiating include blocking and initiating using an electrode unit disposed within the blood vessel of the subject.

In an application, the nerve tissue includes a renal nerve of the subject, the blood vessel includes a renal artery of the subject, and blocking and initiating include blocking and initiating using an electrode unit disposed within the renal artery of the subject.

In an application, the factor includes a factor indicative of a blood pressure of the subject, detecting the first value includes detecting a first value of the factor indicative of the blood pressure of the subject, and detecting the second value includes detecting a second value of the factor indicative of the blood pressure of the subject.

In an application:

the method further includes applying ablative energy to a first portion of the nerve tissue of the subject, initiating the unidirectional action potentials during the second period includes initiating the unidirectional action potentials in a second portion of the nerve tissue by applying a first application of the excitatory current to the second portion of the nerve tissue prior to the application of ablative energy, and detecting the second value of the factor includes detecting the second value of the factor prior to the application of ablative energy, and the method further includes, during a third period, subsequently to the application of ablative energy, initiating unidirectional action potentials in the nerve tissue by applying a second application of the excitatory current to the second portion of the nerve tissue and, after the start of the second application of the excitatory current, detecting a third value of the factor indicative of the parameter of the subject.

In an application:

applying ablative energy includes applying a first application of ablative energy, and the method further includes, at least in part responsively to the second value and the third value, applying a second application of ablative energy to the first portion of the nerve tissue of the subject.

In an application, applying the second application of ablative energy includes applying the second application of ablative energy at least in part responsively to the first value.

In an application, applying the second application of ablative energy includes applying a second application of ablative energy that has an intensity different from an intensity of the first application of ablative energy.

There is further provided, in accordance with an application of the present invention, a method for use with a renal artery of a subject, the renal artery including nerve tissue, the method including:

ablating a lesion in the renal artery of the subject;

initiating first unidirectional action potentials on a first side of the lesion, such that the action potentials propagate toward the lesion; and initiating second unidirectional action potentials on a second side of the lesion, such that the action potentials propagate toward the lesion.

The present invention will be more fully understood from the following detailed description of applications thereof, taken together with the drawings, in which:

BRIEF DESCRIPTION OF THE DRAWINGS

FIGS. 2A-H are schematic illustrations of a technique for facilitating ablation of nerve tissue of the blood vessel of the subject, in accordance with some applications of the invention;

FIG. 4 is a flow diagram of at least some steps in the techniques described with reference to FIGS. 2A-H and 3.

DETAILED DESCRIPTION OF EMBODIMENTS

Figure 1:
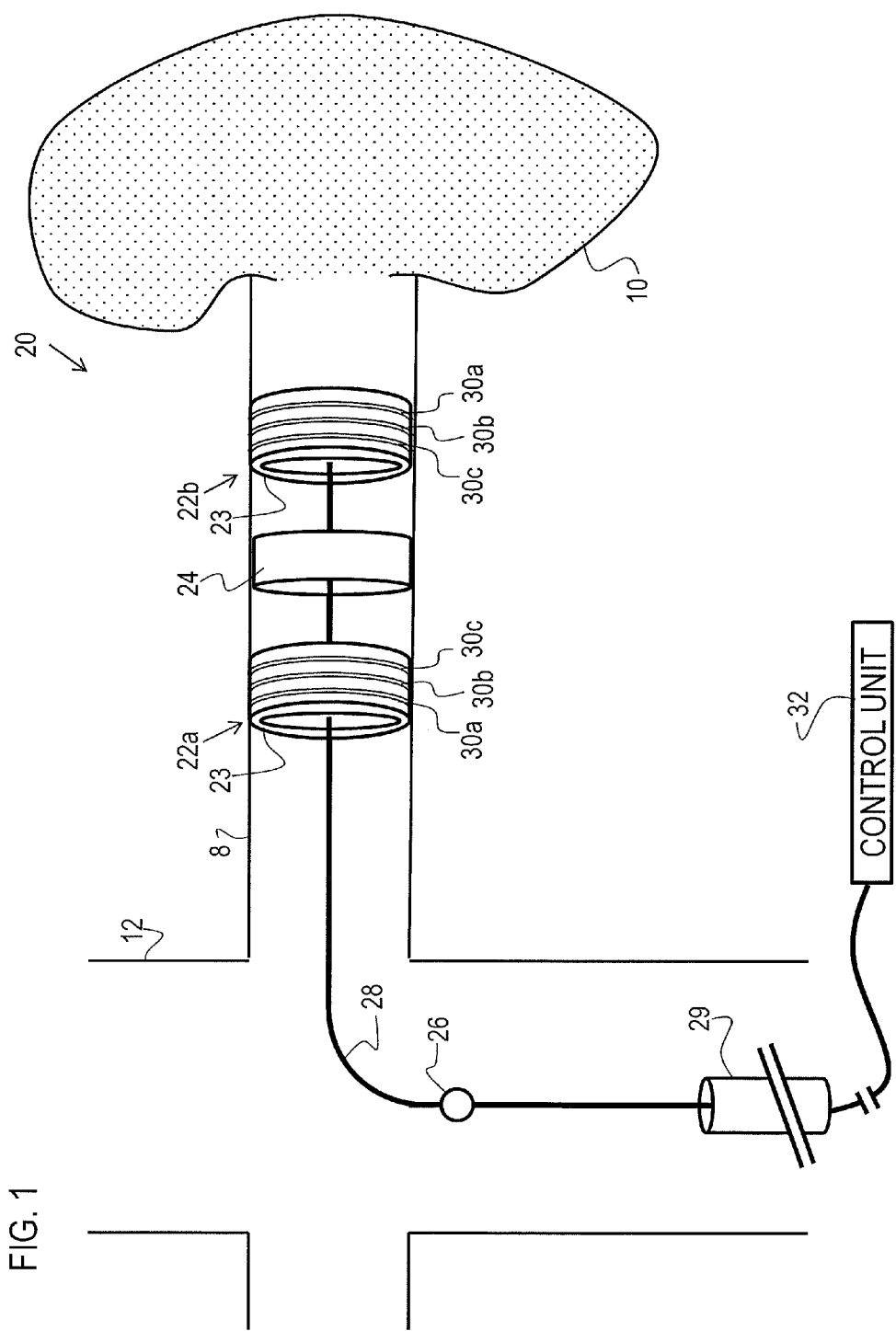
FIG. 1 is a schematic illustration of a system for ablating nerve tissue of a blood vessel of a subject, in accordance with some applications of the invention.

Reference is made to FIG. 1, which is a schematic illustration of a system 20 for ablating nerve tissue of a blood vessel of a subject, in accordance with some applications of the invention. System 20 comprises at least one electrode unit 22, an ablation unit 24, and a sensor 26. Sensor 26 is configured to detect a parameter of the subject, such as a parameter indicative of blood pressure and/or blood flow. Ablation unit 24 is configured to ablate the nerve tissue of the blood vessel, so as to block endogenous action potentials from propagating through the nerve tissue (e.g., to ablate nerve tissue in a first portion of the nerve tissue, so as to permanently block pathogenic action potentials from propagating past the first portion of the nerve tissue). Electrode unit 22 is configured to apply a non-ablative electrical current to the nerve tissue, typically so as to initiate and/or block action potentials in the nerve tissue (e.g., to apply the non-ablative electrical current to a second portion of the nerve tissue, so as to initiate and/or temporarily block action potentials in the second portion of the nerve tissue). Typically, when electrode unit 22 is configured to initiate action potentials in the nerve tissue, it is configured to initiate action potentials that have similar characteristics and/or effects as the endogenous action potentials that the ablation unit is configured to block by ablating the nerve tissue. The parameter that sensor is configured to detect is typically a parameter that changes in response to action potentials in the nerve tissue (e.g., in response to the endogenous action potentials and the induced action potentials, and in response to the blocking of the endogenous action potentials). That is, sensor 26 is configured to detect a physiological response to electrode unit 22 blocking the endogenous action potentials and/or initiating the induced action potentials, and/or to ablation unit 24 ablating the nerve tissue, and thereby blocking the action potentials.

Typically, at least electrode unit 22 and ablation unit 24 are coupled to a single longitudinal member 28, such as a catheter, and member 28, electrode unit 22, and ablation unit 24 are advanceable together, such as within and/or through a sheath 29. For some applications, and as shown in FIG. 1, sensor 26 is also coupled to longitudinal member 28 and is advanceable therewith.

For some applications, and as shown in FIG. 1, system 20 comprises two electrode units 22 (e.g., electrode unit 22a and electrode unit 22b). Electrode unit 22a is disposed proximally from ablation unit 24, and electrode unit 22b is disposed distally from ablation unit 24. Typically, each electrode unit 22 is configured to initiate unidirectional action potentials in the nerve tissue, such as by providing an excitatory current adjacent to a blocking current, e.g., as is known in the nerve cuff art. For example, each electrode unit 22 may comprise three or more electrodes 30 (e.g., electrodes 30a, 30b, and 30c), electrodes 30a and 30b being driven (e.g., by a control unit 32) to apply a non-ablative blocking current, such as a high-frequency (HF) blocking current, and electrode 30c being driven to apply an excitatory current that initiates action potentials that thereby propagate only in the direction away from the other two electrodes (i.e., the action potentials are blocked from propagating past the other two electrodes). Typically, the excitatory current has a lower frequency than the blocking current. When each electrode unit 22 is configured to initiate unidirectional action potentials, the electrode units are oriented on longitudinal member 28 such that the unidirectional action potentials initiated by each electrode unit propagate toward the nerve tissue that is adjacent to ablation unit 24 (e.g., toward the first portion of the nerve tissue).

For applications in which system 20 comprises two electrode units, the electrode units are thereby also oriented such that the unidirectional action potentials initiated by each electrode unit propagate toward the other electrode unit. For applications in which system 20 comprises only one electrode unit, that electrode unit may comprise electrode unit 22a or 22b (e.g., that electrode unit may be disposed in the position and/or orientation described for electrode unit 22a or 22b). It should be noted that, although control unit 32 is shown in FIG. 1 as being outside of the blood vessel(s) in which the electrode units and ablation unit are disposed (e.g., outside the body of the subject), for some applications, control unit 32 and/or other controllers are configured to be intracorporeal (e.g., to be disposed within the blood vessel(s) in which the electrode units and ablation unit are disposed).

For some applications, ablation unit 24 comprises one or more electrodes, and is configured to ablate the nerve tissue by applying radio frequency (RF) current to the nerve tissue (e.g., by comprising an RF ablation unit that is configured to be driven by control unit 32 to apply the RF current). For some applications, ablation unit 24 comprises one or more ultrasound transducers, and is configured to ablate the nerve tissue by applying ultrasound energy to the nerve tissue (e.g., by comprising an ultrasound ablation unit that is configured to be driven by control unit 32 to apply the ultrasound energy). Ablation unit 24 may alternatively or additionally be configured to ablate the nerve tissue cryogenically, using laser, using resistive heating, using chemical ablation, or via another ablation mechanism.

Reference is now made to FIGS. 1 and 2A-H, FIGS. 2A-H being schematic illustrations of a technique for facilitating ablation of nerve tissue of the blood vessel of the subject using system 20, in accordance with some applications of the invention. In FIGS. 1 and 2A-H, the blood vessel comprises a renal artery 8 of the subject, disposed between a kidney 10 and the aorta 12 (e.g., the abdominal aorta) of the subject, and system 20 is configured to ablate nerve tissue of the renal artery, so as to treat hypertension. However, for other applications, system 20 may be used to ablate nerve tissue of another blood vessel, such as the carotid artery (e.g., the carotid sinus) or the aortic arch. For example, hypertension may alternatively or additionally be treated by ablation of chemoreceptors and/or baroreceptors in the carotid sinus, and/or nerve tissue associated therewith, and/or ablation of sympathetic nerve tissue of the aortic arch. Furthermore, system 20 may be used to ablate nerve tissue at other sites, such as at a pulmonary vein ostium.

System 20 is advanced percutaneously (e.g., transluminally, such as transfemorally) such that at least electrode units 22a and 22b, and ablation unit 24 are disposed within renal artery 8. Thereby, electrode units 22a and 22b, and ablation unit 24 are adjacent to respective portions of the nerve tissue of the renal artery. Typically, sensor 26 is configured to detect a parameter indicative of blood pressure of the subject (e.g., sensor 26 may comprise a pressure sensor). Typically, sensor 26 is coupled to longitudinal member 28 such that when the electrode units and ablation unit are disposed in renal artery 8, the sensor is disposed in aorta 12. Alternatively, system 20 may be configured such that sensor 26 is disposed in renal artery 8. Sensor 26 may alternatively be configured to detect a parameter indicative of blood flow of the subject. For example, sensor 26 may comprise an ultrasound transceiver, configured to detect the blood flow using Doppler ultrasound. For some such applications, sensor 26 may be extracorporeal (e.g., not coupled to longitudinal member 28).

Following delivery to renal artery 8, electrode units 22a and 22b are typically expanded from a compressed delivery state, to an expanded state in which electrodes 30 are placed in contact with the wall of the renal artery, and in which fluid communication is maintained between the aorta 12 and kidney 10. For example, and as shown in FIGS. 1 and 2A-H, each electrode unit may comprise a tubular element 23, such as a stent, on which electrodes 30 are disposed. Alternatively, each electrode unit may comprise discrete "lasso"-type electrodes that are not coupled to a tubular element. For some applications (e.g., for applications in which ablation unit 24 comprises an RF ablation unit), ablation unit 24 is also expanded from a compressed delivery state to an expanded state thereof. For some such applications, electrode units 22 and ablation unit 24 are disposed on a single tubular element, and/or comprise an integrated device. Alternatively (e.g., for applications in which ablation unit 24 comprises an ultrasound ablation unit), ablation unit 24 is not expanded (e.g., does not require contact with the wall of renal artery 8).

FIGS. 2A-H show sequential steps in a technique of ablating nerve tissue of renal artery 8, using system 20, in accordance with some applications of the invention. Each of FIGS. 2A-H shows a state of system 20 for a respective step, and a corresponding illustrative chart of blood pressure detected up until, and including, the respective step.

Figure 2A:
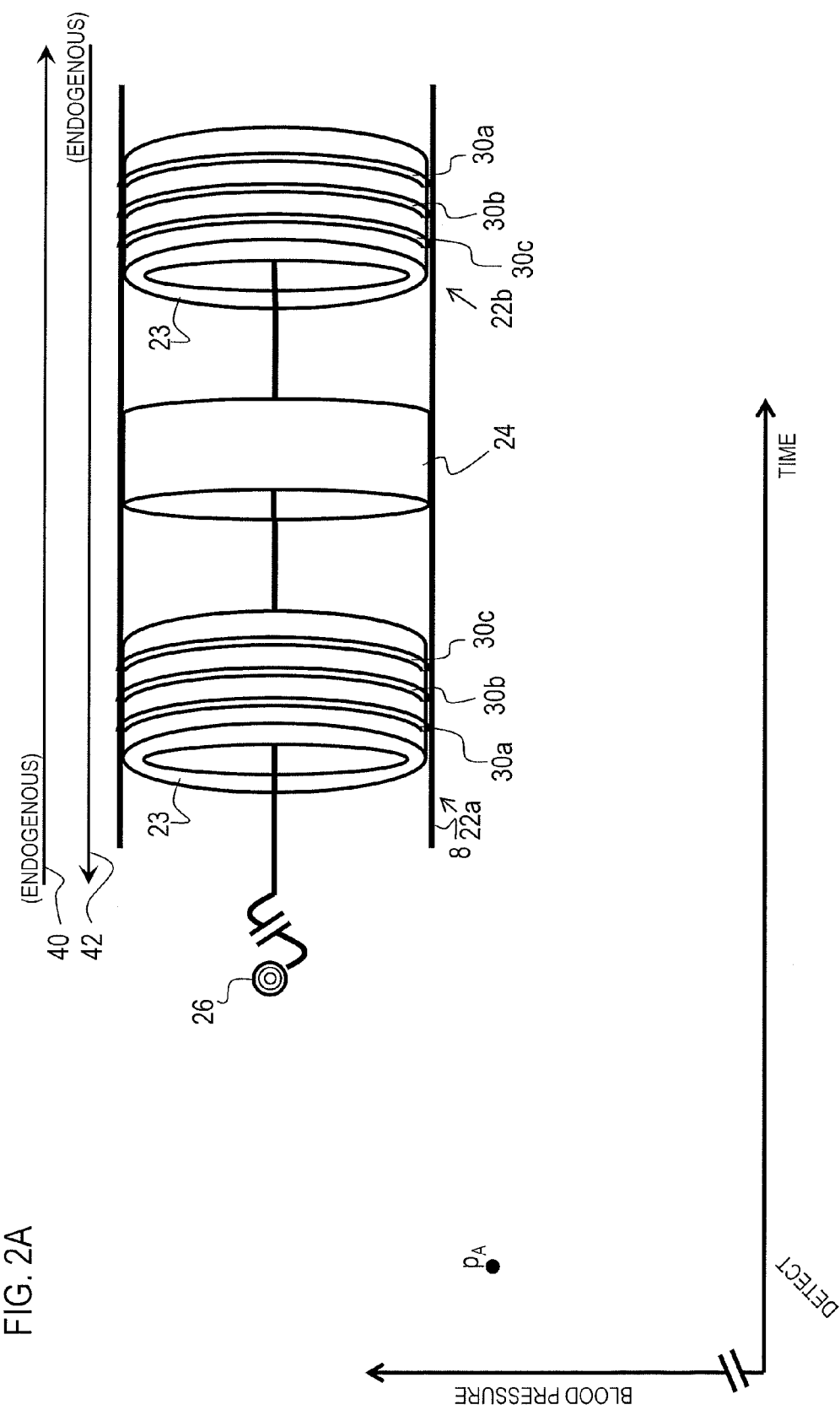

Following placement of system 20 in the body of the subject (e.g., as described hereinabove), sensor 26 detects a blood pressure p_A of the subject (FIG. 2A). For some applications, detected blood pressure p_A represents an "untreated" blood pressure. Endogenous efferent action potentials 40 and endogenous afferent action potentials 42 are shown propagating along nerve tissue of renal artery 8 (e.g., between kidney 10 and the central nervous system (CNS) of the subject). It is to be noted that blood pressure p_A, and the other detected blood pressures described herein, are typically each detected while the subject is in the same state (e.g., reclining and/or sedated), so as to reduce variability.

FIG. 2B shows electrode units 22a and 22b each applying a non-ablative blocking current to the nerve tissue of renal artery 8. It is to be noted that throughout the specification, the blocking current is referred to as the "non-ablative blocking current," so as to be distinct from any current of ablative energy applied by the ablation unit, which may otherwise be considered a "blocking current" because of the blocking effect of the resulting ablation. It is to be further noted that, although the excitatory current applied by the electrode units is also non-ablative, it is generally referred to as the "excitatory current".

As described hereinabove, for some applications, the electrode units drive the non-ablative blocking current via electrodes 30a and 30b. For some applications, only one of the electrode units applies the non-ablative blocking current. Endogenous efferent action potentials 40 and endogenous afferent action potentials 42 are shown being blocked from propagating along nerve tissue of renal artery 8, by the non-ablative blocking current. It is hypothesized that this blocking of endogenous action potentials has similar effects to ablation of nervous tissue of the renal artery (e.g., to decrease systemic blood pressure), as is known in the art.

After the start of the application of the non-ablative blocking current (e.g., while the non-ablative blocking current is being applied, or after it has stopped being applied) sensor 26 detects a blood pressure p_B of the subject. (In general, sensing may also be performed at any other time, e.g., continuously.) For example, the blood pressure may be detected after a duration in which blood pressure is allowed to respond to the reduction in renal nerve activity. The non-ablative blocking current may be calibrated in real-time (e.g., by adjusting amplitude, frequency and/or duty cycle), so as to establish the current that results in the lowest blood pressure in the subject. In general, p_B represents a hypothetical lowest blood pressure achievable by a hypothetical perfect ablation of the nerve tissue of renal artery 8, that blocks all action potentials from propagating therealong.

FIG. 2C shows electrode units 22a and 22b initiating respective action potentials 50 and 52 (i.e., induced action potentials) in the nerve tissue of renal artery 8, by applying an excitatory current to the nerve tissue. As described hereinabove, for some applications, each electrode unit drives the excitatory current via electrode 30c. As also described hereinabove, the electrode units are typically configured to initiate unidirectional action potentials, and are oriented such that the unidirectional action potentials propagate toward the nerve tissue adjacent to ablation unit 24 and toward the other electrode unit. That is, (1) action potentials 50, initiated by electrode unit 22a are typically efferent, and propagate from unit 22, past ablation unit 24, and toward kidney 10, and (2) action potentials 52, initiated by electrode unit 22b are typically afferent, and propagate from unit 22, past ablation unit 24, and toward aorta 12 and the CNS of the subject.

It is hypothesized that, by contrast to the blocking of endogenous action potentials, initiation of action potentials 50 and 52 has similar effects to increased endogenous action potentials (e.g., to increase systemic blood pressure). For example, it is hypothesized that action potentials 50 induce kidney 10 to increase systemic blood pressure via the sympathetic pathway, and action potentials 52 induce the CNS to increase systemic blood pressure via the sympathetic pathway. It is further hypothesized that the magnitude of the effects of action potentials 50 and 52 may be greater than those of the endogenous action potentials, and/or that action potentials 50 and 52 are configurable to have such greater effects.

After the start of the application of the excitatory current (e.g., while the excitatory current is being applied, or after it has stopped being applied), sensor 26 detects a blood pressure p_C of the subject. For example, the blood pressure may be detected after a duration in which blood pressure is allowed to respond to the increase in renal nerve activity. The excitatory current may be calibrated in real-time (e.g., by adjusting amplitude, frequency and/or duty cycle), so as to establish the current that results in the highest blood pressure in the subject. For some applications, p_C represents a hypothetical highest blood pressure achievable by a high-level (e.g., hypothetical maximum) renal nerve activity (e.g., the highest blood pressure achievable by the body of the subject via renal nerve activity).

Although FIG. 2C shows two opposite-facing unidirectional electrode units, it is noted that for some applications, only one electrode unit is used, and for some applications, the electrode unit(s) are not unidirectional. For applications in which two electrode units are used, the operation of the electrode units may be temporally offset with respect to each other, so as to reduce interference therebetween. For example, although on a relatively large timescale, electrode unit 22a may initiate induced action potentials 50 at generally the same time as electrode unit 22b initiates induced action potentials 52, nevertheless, on a relatively small timescale, the action potentials are typically alternated (e.g., as indicated by action potentials 50 and 52 being labeled as being applied at "time=t" and "time=t+delta t", respectively).

It is to be noted that, although FIGS. 2A-H show sequential steps, the steps described with reference to FIGS. 2A-C may be performed in a different order (e.g., the step described with reference to FIG. 2C may be performed before the step described with reference to FIG. 2B).

Figure 2D:
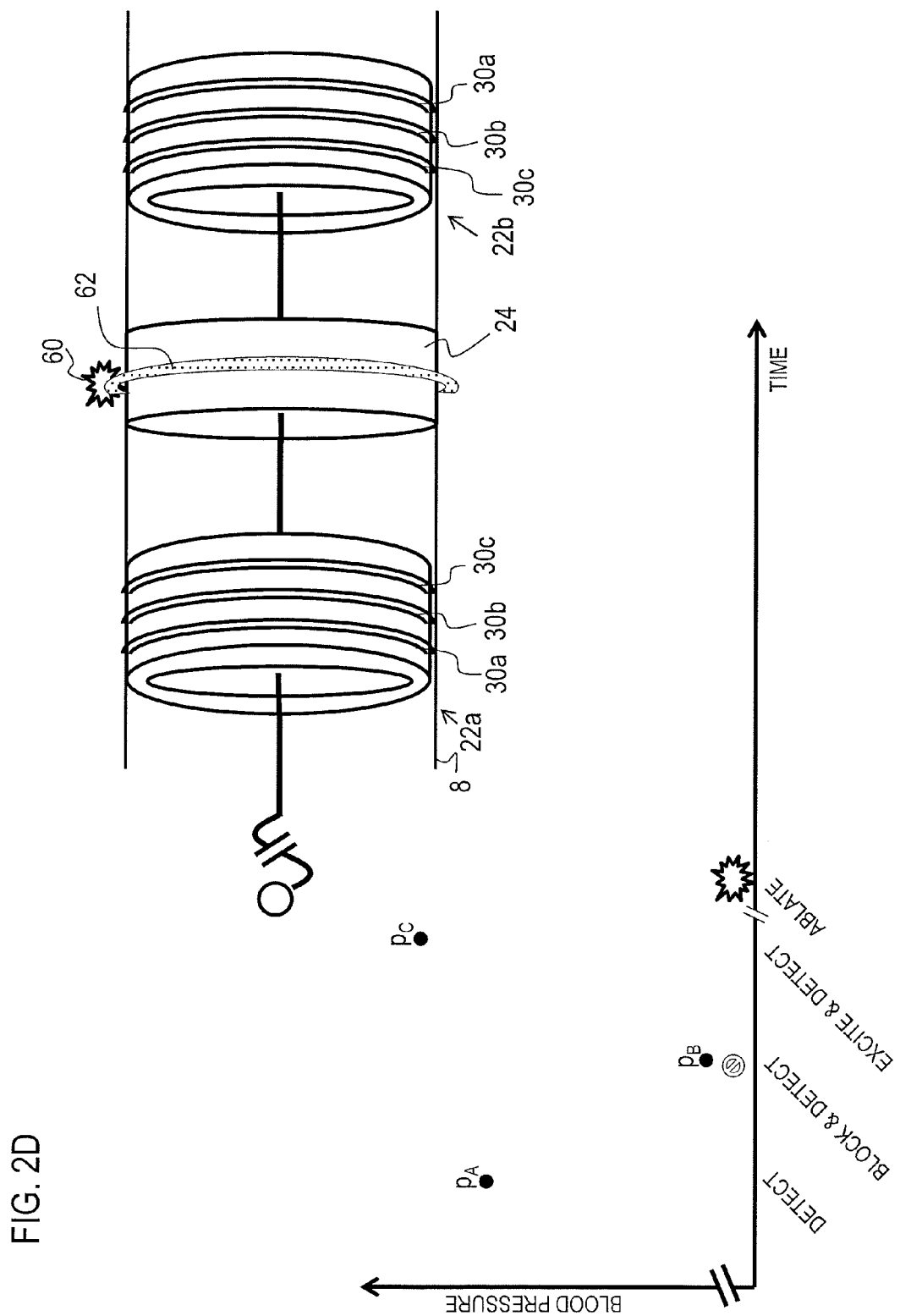

FIG. 2D shows ablation unit 24 applying a first application of ablative energy 60 (e.g., ablating RF energy) to the nerve tissue of renal artery 8. It is desirable to ablate renal artery tissue to a degree that is sufficient to achieve a desired decrease of renal nerve activity, but not to a greater degree. The first application of ablative energy 60 is typically configured to be insufficient to ablate the nerve tissue to the desired degree (e.g., insufficient to completely ablate the nerve tissue). For example, first application 60 may be configured to be sufficient to fully ablate nerve tissue in less than 50% (e.g., less than 20%, such as less than 10%) of the general population. That is, first application 60 generates, in the wall of renal artery 8, a lesion 62 (e.g., a circumferential lesion) that is sufficient to completely block renal nerve activity in less than 50% (e.g., less than 20%, such as less than 10%) of the general population.

FIG. 2D does not show the non-ablative blocking current being applied by electrode units 22a and 22b during the application of the ablative energy by ablating unit 24. However, for some applications, the non-ablative blocking current is applied at this time. For some such applications, the application of the non-ablative blocking current during the application of the ablative energy reduces pain experienced by the subject, e.g., by inducing local paresthesia and/or anesthesia. The non-ablative blocking current that is used to induce this pain relief may have the same characteristics as, or different characteristics from, the non-ablative blocking current used to block endogenous signals in the nerve tissue being ablated. For some applications, a distinct electrode unit is used for application of the pain-relieving non-ablative blocking current. For some applications, another pain-relief method (e.g., providing an analgesic drug) is alternatively or additionally used.

Figure 2E:
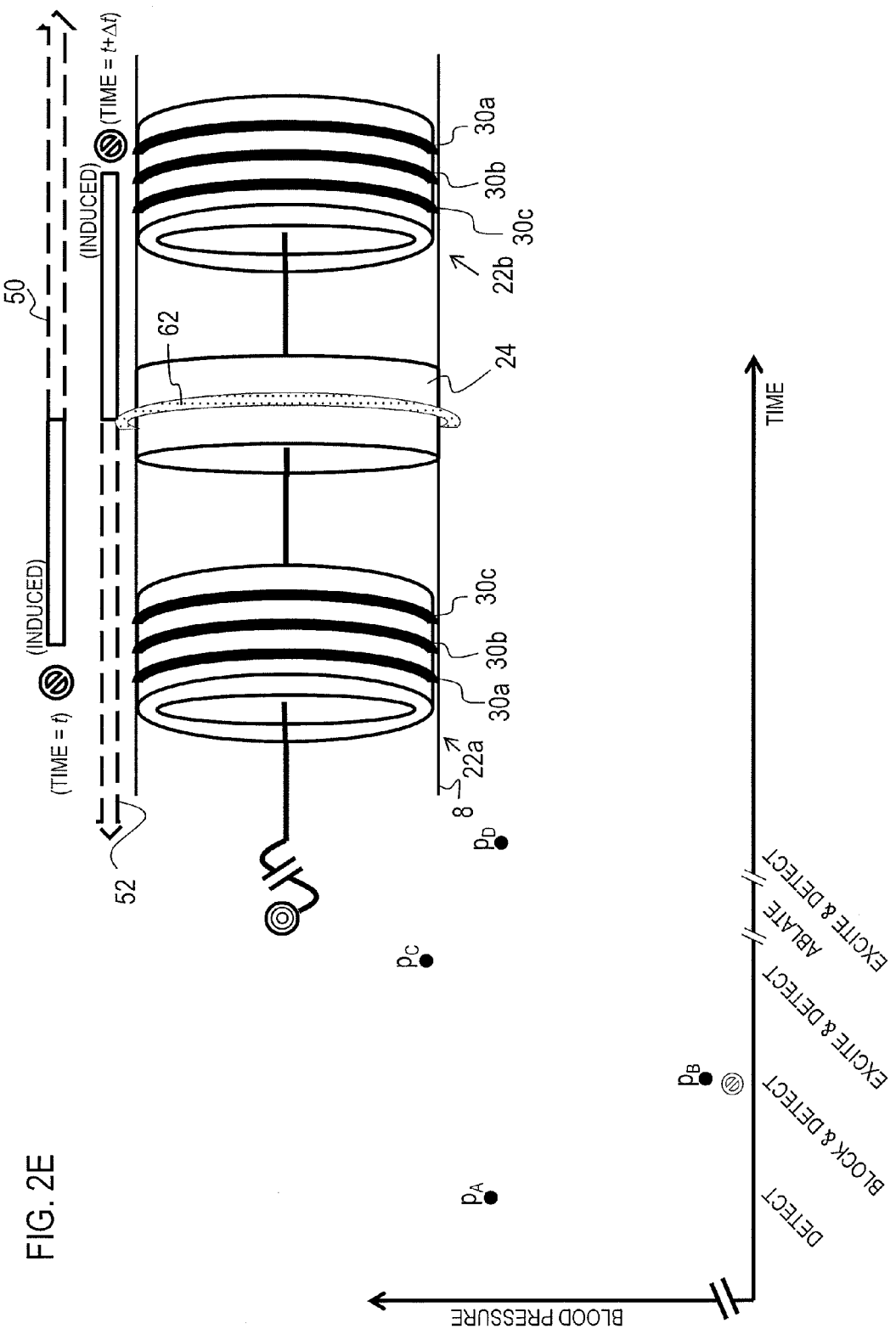

Subsequent to first application 60, electrode units 22a and 22b again initiate induced action potentials 50 and 52, by again applying the excitatory current (FIG. 2E). Action potentials 50 and 52 are at least in part blocked from propagating past lesion 62 in the nerve tissue (illustrated by the portions of the arrows of the action potentials that are disposed past lesion 62 being broken). After the start of the application of the excitatory current (e.g., while the excitatory current is being applied, or after it has stopped being applied) sensor 26 detects a blood pressure p_D of the subject. For example, the blood pressure may be detected after a duration in which blood pressure is allowed to respond to action potentials 50 and 52. Detected blood pressure p_D may thereby represent a hypothetical highest blood pressure achievable by a high-level (e.g., hypothetical maximum) renal nerve activity, following first application of ablative energy (e.g., a high-level (e.g., hypothetical maximum) renal nerve activity in the presence of lesion 62). Due to the reduced propagation of induced action potentials 50 and 52 caused by lesion 62, detected blood pressure p_D is typically lower than detected blood pressure p_C. Pressure p_D is typically greater than pressure p_B (e.g., due to the typical configuration of first application of ablative energy 60 to be typically insufficient to completely ablate the nerve tissue).

Subsequently, ablation unit 24 typically applies a second application of ablative energy 60' to the nerve tissue of renal artery 8, thereby increasing the degree of ablation of the lesion (now designated 62' (FIG. 2F)). Second application 60' may have the same characteristics (e.g., intensity) as first application 60, or may be different (e.g., may have a greater or lower intensity). For example, if sensor 26 determines that the reduction in systemic blood pressure due to first application of ablative energy 60 is significantly less than is desired, then second application of ablative energy 60' may be set to have a higher intensity than first application of ablative energy 60. Similarly, if sensor 26 determines that the reduction in systemic blood pressure due to first application of ablative energy 60 is close to a desired level, then second application of ablative energy 60' may be set to have an equal or lower intensity than first application of ablative energy 60. (In general, the intensity of applied energy may be varied using techniques known in the art, such as by varying amplitude, pulse width, frequency, duration of energy application, or duty cycle of energy application.)

Figure 2G:
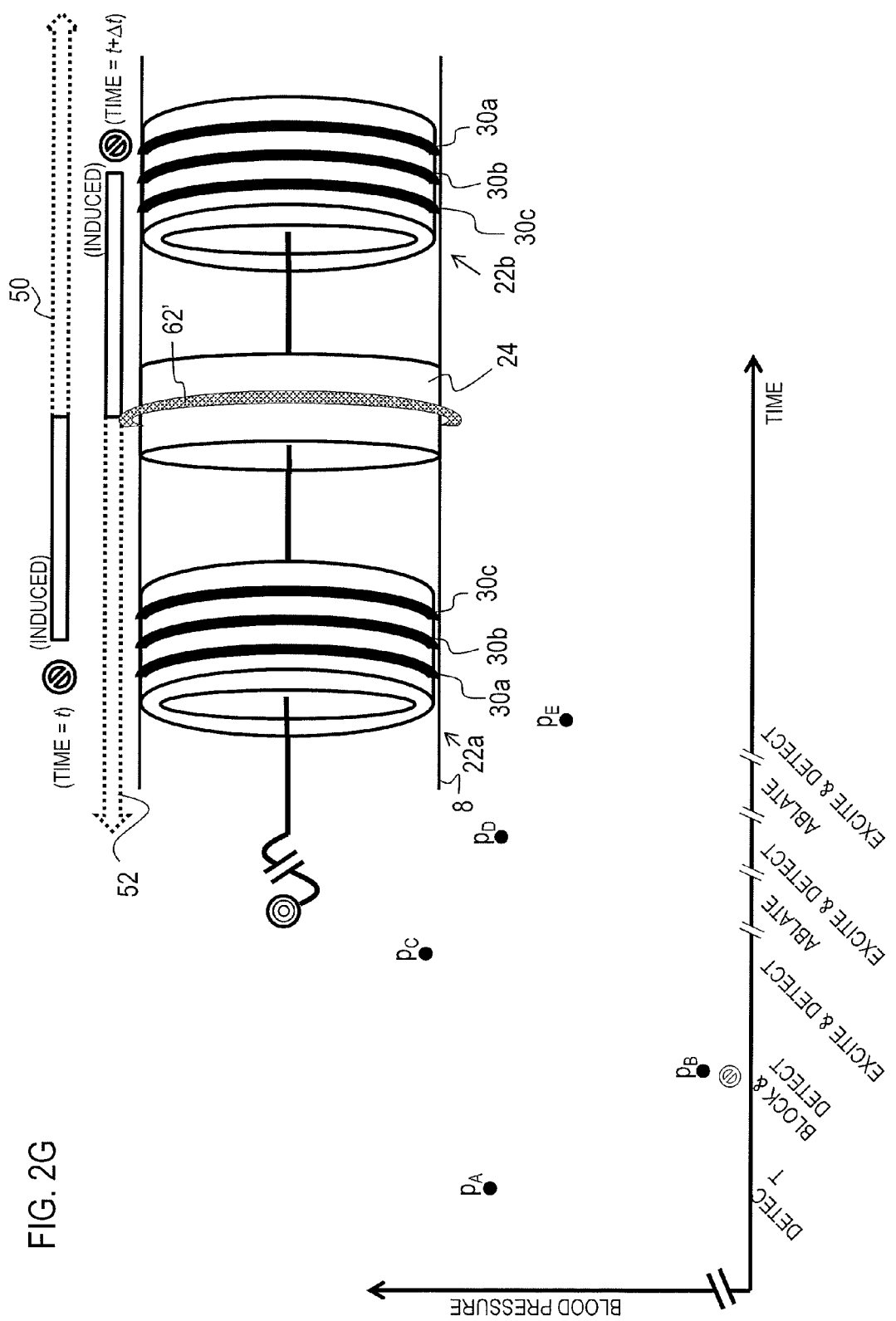

Subsequent to second application of ablative energy 60', electrode units again initiate action potentials 50 and 52 by applying the excitatory current (FIG. 2G). Due to the increased ablation of the lesion, action potentials 50 and 52 are blocked from propagating past lesion 62', to a greater degree than they were from propagating past lesion 62 (illustrated by the broken portions of the arrows of the action potentials in FIG. 2G, being more broken than the same portions in FIG. 2G). After the start of the application of the excitatory current (e.g., while the excitatory current is being applied, or after it has stopped being applied) sensor 26 detects a blood pressure p_E of the subject. For example, the blood pressure may be detected after a duration in which blood pressure is allowed to respond to action potentials 50 and 52. Detected blood pressure p_D may thereby represent a hypothetical highest blood pressure achievable by a high-level (e.g., hypothetical maximum) renal nerve activity, following second application of ablative energy 60' (e.g., a high-level (e.g., hypothetical maximum) renal nerve activity in the presence of lesion 62'). Due to the further reduced propagation of induced action potentials 50 and 52 caused by lesion 62', detected blood pressure p_E is typically lower than detected blood pressure p_D.

Figure 2H:
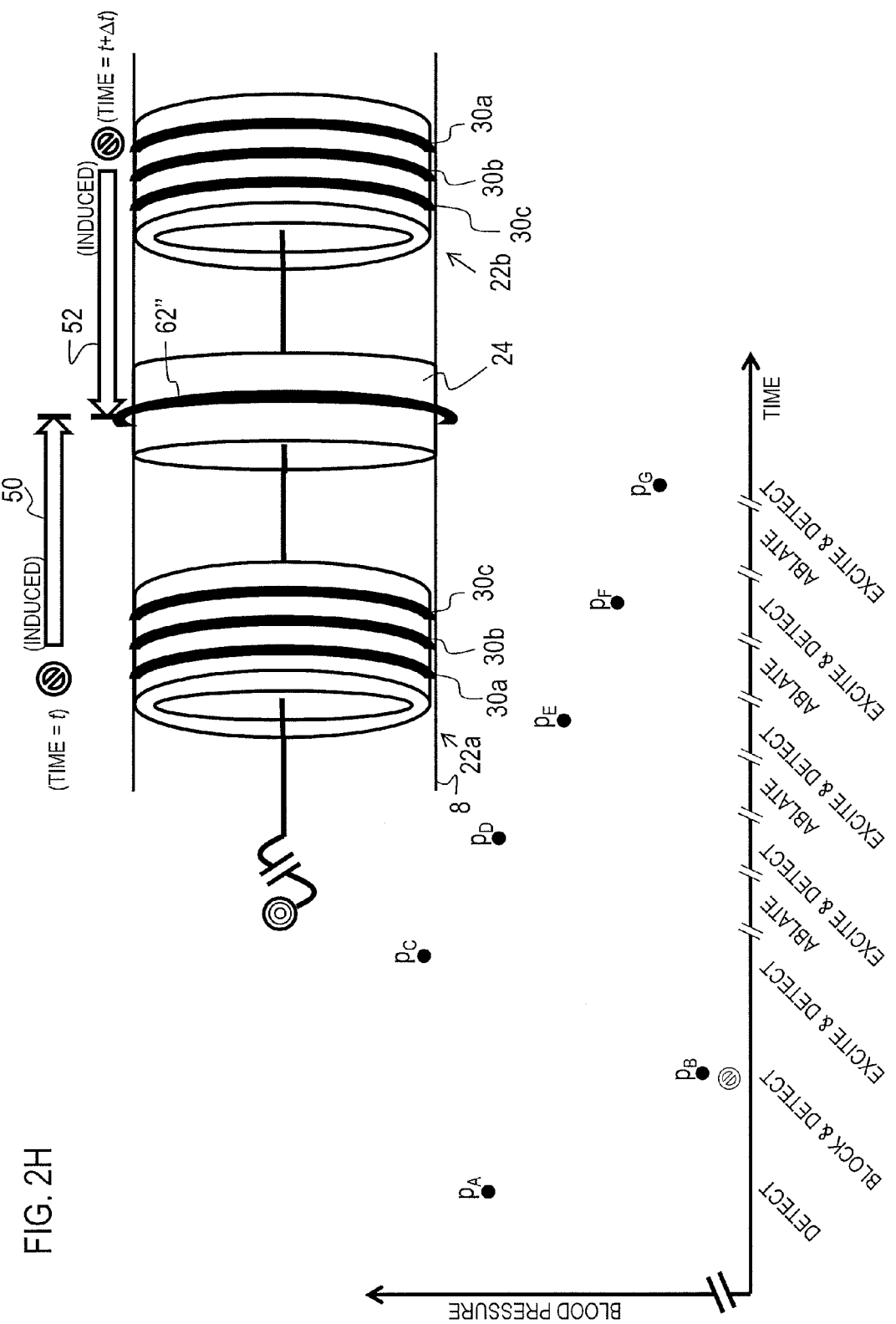

The cycle of ablating nerve tissue, initiating action potentials, and detecting blood pressure (e.g., as described with reference to FIGS. 2D-E, and FIGS. 2F-G) may be repeated as necessary. FIG. 2H shows an example in which a further two such cycles have been performed, and respective detected blood pressures p_F and p_G have been obtained. Induced action potentials 50 and 52 are completely blocked from propagating past the lesion, which is now designated 62". It is to be noted that, for some applications and/or for some subjects, fewer or more cycles may be useful to achieve a desired degree of blocking (e.g., complete blocking). For example, for some subjects, only one application of ablation energy is applied.

Reference is again made to FIGS. 2A-H. For some applications, impedance between electrode units 22a and 22b is measured at each cycle, so as to further facilitate the determination of the achieved degree of ablation.

Figure 3:
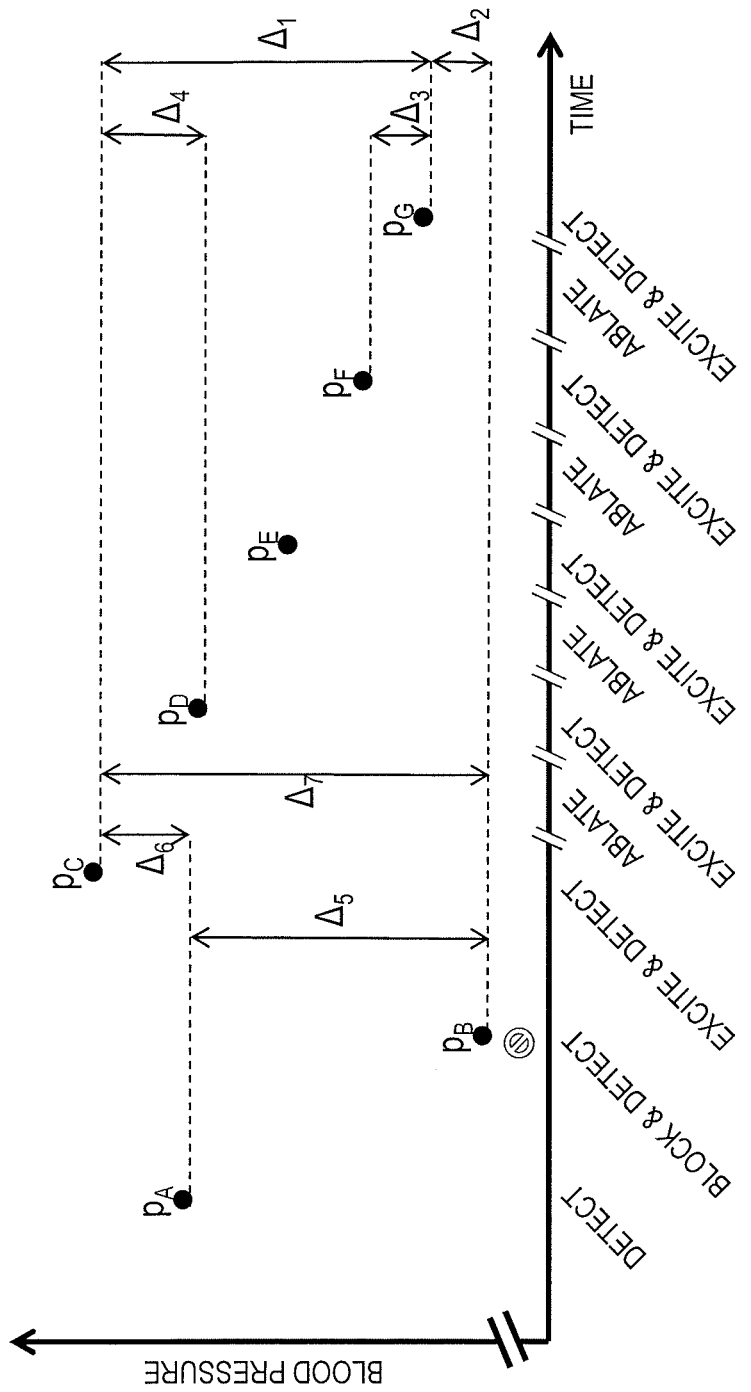
FIG. 3, is a schematic illustration of some techniques for facilitating ablation of nerve tissue of the renal artery, in accordance with some applications of the invention.

Reference is made to FIG. 3, which is a schematic illustration of some techniques for facilitating ablation of nerve tissue of the renal artery, in accordance with some applications of the invention. FIGS. 2A-H show a technique of using system 20 to repeatedly (e.g., cyclically) initiate induced action potentials in, and ablate, nerve tissue of the renal artery, and to repeatedly detect blood pressure of the subject (1) in the presence and absence of the induced action potentials, and (2) before and after the ablations. As described with reference to FIGS. 2A-H, this ablate-excite-detect cycle may be repeated as necessary to achieve a desired degree of ablation. FIG. 3 shows several techniques by which a suitable number of repetitions may be determined. Typically, this determination is performed after each detection of blood pressure subsequent to detection of blood pressure p_A. For illustrative purposes, FIG. 3 shows this determination being performed after four ablations and four respective blood pressure detections (p_D, p_E, p_F, and p_G).

For some applications, the ablate-excite-detect cycle is stopped at least in part responsively to the difference delta_1 between detected blood pressure p_G and detected blood pressure p_C. For example, difference delta_1 may be the difference between (1) the blood pressure detected after the most recent application of ablation energy, and (2) the highest blood pressure achievable by the high-level (e.g., hypothetical maximum) renal nerve activity.

For some applications, the ablate-excite-detect cycle is stopped at least in part responsively to the difference delta_2 between detected blood pressure p_G and detected blood pressure p_B. For example, difference delta_2 may be the difference between (1) the blood pressure detected after the most recent application of ablation energy, and (2) the hypothetical lowest blood pressure achievable by the hypothetical perfect ablation of the nerve tissue of the renal artery. For some such applications, the cycle is stopped at least in part responsively to a difference in magnitude between difference delta_1 and difference delta_2. For example, if delta_1 is significantly greater (e.g., more than a threshold magnitude greater) than delta_2, the cycle may be stopped because a threshold proportion of a hypothetical possible effect on blood pressure is deemed to have already been induced.

It is hypothesized that delta_1 and delta_2 are indicative of the cumulative effect of the ablations up to, and including, the most recent ablation, on the maximum possible contribution by renal nerve activity to blood pressure.

For some applications, the ablate-excite-detect cycle is stopped at least in part responsively to the difference delta_3 between detected blood pressure p_G and detected blood pressure p_F. For example, difference delta_3 may be the difference between (1) the blood pressure detected after the most recent application of ablation energy, and (2) the blood pressure detected after the immediately-prior application of ablation energy. For some such applications, the cycle is stopped at least in part responsively to the difference delta_4 between detected blood pressure p_D and detected blood pressure p_C. For example, difference delta_4 may be the difference between (1) the blood pressure detected after the first application of ablation energy, and (2) the blood pressure detected before the first application of ablation energy. For some such applications, the cycle is stopped at least in part responsively to a difference in magnitude between difference delta_3 and difference delta_4. For example, if delta_3 is significantly smaller (e.g., more than a threshold magnitude smaller) than delta_4, the cycle may be stopped because it is deemed that the most recent application of ablative energy (i.e., that which resulted in difference delta_4) was significantly less effective in reducing blood pressure than was the first application of ablative energy, and thereby further applications of ablative energy are also unlikely to be significantly effective.

It is hypothesized that delta_3 and delta_4 are indicative of the effect of the most recent ablation, and the first ablation, respectively, on the maximum possible contribution by renal nerve activity to blood pressure. It is thereby hypothesized that delta_4 alone, and when compared to delta_3, is indicative of the efficacy of the most recent application of ablation energy.

For some applications, at least in part responsively to one or more blood pressure detections, no ablation is performed. For example, if, in a given subject, a difference delta_5 between detected "untreated" blood pressure p_A and the hypothetical lowest blood pressure achievable by the hypothetical perfect ablation of the nerve tissue p_B, is lower than a threshold difference, it may be determined that renal nerve ablation is not an appropriate treatment for that subject. A similar determination may be made alternatively or additionally in response to (1) a difference delta_6 between blood pressure p_A and blood pressure p_C, and/or (2) a difference delta_7 between blood pressure p_C and blood pressure p_B. It is hypothesized that differences delta_5, delta_6, and/or delta_7 are indicative of the potential efficacy of renal nerve ablation on hypertension for the given subject, and thereby, at least in part responsively to these differences, patient selection may be performed. For example, a high value of delta_7 may be indicative of a relatively high sensitivity of blood pressure to renal nerve activity in the given subject, and therefore the given subject is more likely to be selected for renal nerve ablation.

It is to be noted that, for some applications, one or more of the blood pressure measurements described hereinabove may be omitted from the procedure. For example, if it is known in advance which of differences delta_1 through delta_7 are to be used to determine when to stop the ablate-excite-detect cycle, a measurement that is not to be used may be omitted. Typically, however, only a maximum of two of the pre-ablation blood pressures (e.g., p_A, p_B, and p_C) are omitted, and none of the post-ablation blood pressures (e.g., p_D, p_E, p_F, and p_G) are omitted. For some applications, the determination of when to stop the ablate-excite-detect cycle is based solely on the blood pressure achieved following the most recent ablation.

Reference is made to FIG. 4, which is a flow diagram, illustrating at least some steps in the techniques described with reference to FIGS. 2A-H and 3. Step 102 comprises detecting a preliminary value of a parameter indicative of blood pressure, e.g., as described with reference to FIG. 2A.

Step 104 comprises (1) blocking endogenous action potentials in the nerve by applying a non-ablative blocking current to the nerve and (2) after the start of the application of the non-ablative blocking current, detecting a value of the parameter (i.e., a "blocked" value), e.g., as described with reference to FIG. 2B. The "blocked" value may be greater or smaller than the preliminary value, depending on the parameter and nerve being ablated. For example, for applications in which the renal nerve is being ablated so as to treat hypertension, blocking of endogenous action potentials in the renal nerve typically reduces blood pressure. As also described with reference to FIG. 2B, a calibration step 106 is optionally performed, so as to establish the characteristics of the non-ablative blocking current that will have the greatest effect on the detected parameter.

Step 108 comprises (1) initiating action potentials in the nerve by applying an excitatory current to the nerve and (2) after the start of the application of the excitatory current, detecting a value of the parameter (i.e., an "excited" value), e.g., as described with reference to FIG. 2C. Similarly to the "blocked" value, the "excited" value may be greater or smaller than the preliminary value, depending on the parameter and nerve being ablated. As also described with reference to FIG. 2C, a calibration step 110 is optionally performed, so as to establish the characteristics of the non-ablative blocking current that will have the greatest effect on the detected parameter.

As described hereinabove, steps 102, 104, and 106 may be performed in a different order from that shown in FIG. 4. However, step 102 is typically performed subsequent to the delivery of the apparatus (e.g., system 20) into the subject, and prior to steps 104 and 106.

Step 112 comprises ablating the nerve tissue by applying ablative energy, e.g., as described with reference to FIG. 2D (and as subsequently described with reference to FIG. 2F). Subsequently, step 114 is performed, which comprises (1) initiating action potentials in the nerve by applying an excitatory current to the nerve and (2) after the start of the application of the excitatory current, detecting a value of the parameter, e.g., as described with reference to FIG. 2E. For some applications, step 114 is identical to step 108, except that the nerve tissue in which the action potentials are being initiated has been at least in part ablated. The value detected in step 114 is thereby an "ablated" value.

Subsequently, the "ablated" value is compared to at least one of: the preliminary value, the "blocked" value, and the "excited" value (step 116), and a decision 118 to continue ablating, or to stop, is made, e.g., as described with reference to FIG. 3. If it is decided to continue ablating, steps 112, 114, 116, and 118 are repeated, optionally after an adjustment step 120 in which one or more characteristics (e.g., the intensity) of the ablation energy is adjusted. This part of the technique thereby represents a cycle 122, which may comprise the ablate-excite-detect cycle described hereinabove (e.g., with reference to FIGS. 2A-H and 3).

For some applications, the initiation of action potentials and the ablation steps shown in FIG. 4 (e.g., within steps 108 and 114) may be performed using a single electrode unit. For example, a single electrode unit may be moved back and forth through a blood vessel, alternating between applying an excitatory current and applying ablative energy (e.g., an ablating RF current). The single electrode unit may also be used to perform the blocking of endogenous action potentials (e.g., within step 104), by applying a non-ablating blocking current.

Reference is again made to FIGS. 2A-4. System 20, and the techniques described herein, may be performed with varying degrees of automation, in accordance with various applications of the invention. For example:

System 20 may display the blood pressures detected by sensor 26 (e.g., on a display, in numerical and/or graphical format), such that an operating physician may determine when to stop the ablate-excite-detect cycle. For example, a graph similar to that shown in FIG. 4 may be displayed.

System 20, at least in part based on the detected blood pressures, may display an instruction or suggestion to the physician, as to whether to continue or stop the ablate-excite-detect cycle. Similarly, audio instructions/suggestions may be provided by system 20.

System 20 (e.g., control unit 32 thereof) may automatically control the electrode units and ablation unit, at least in part based on the detected blood pressures. For example, control unit 32 may receive, from sensor 26, information indicative of the detected blood pressures, and responsively control (e.g., stop) the ablate-excite-detect cycle.

Reference is again made to FIGS. 2A-4. For some applications of the invention, one or more drugs may be administered to the subject so as to modulate the blood pressure of the subject, in order to facilitate one or more of the steps described hereinabove. For example, a blood pressure-reducing drug may be administered to the subject throughout the entire procedure, so as to reduce all the detected values of blood pressure (e.g., p_A, p_B, etc., shown in FIG. 3). For some such applications, the differences between these detected values (e.g., delta_5, delta_6, etc., shown in FIG. 3) remain relatively constant (i.e., shift, but generally do not change in magnitude) as the detected values change. It is hypothesized that, for some such applications, administering such a blood pressure-reducing drug allows the determination of the hypothetical highest blood pressure achievable by a high-level (e.g., hypothetical maximum) renal nerve activity (e.g., p_C) without increasing the blood pressure of the subject to more than a desired (e.g., safe) threshold. Similarly, a blood pressure-increasing drug may be administered to increase the detected values of blood pressure, such as to allow the determination of the hypothetical lowest blood pressure achievable by a hypothetical perfect ablation of the nerve tissue (e.g., p_B, shown in FIG. 3), without reducing the blood pressure of the subject to below a desired (e.g., safe) threshold.

Figure 5A:
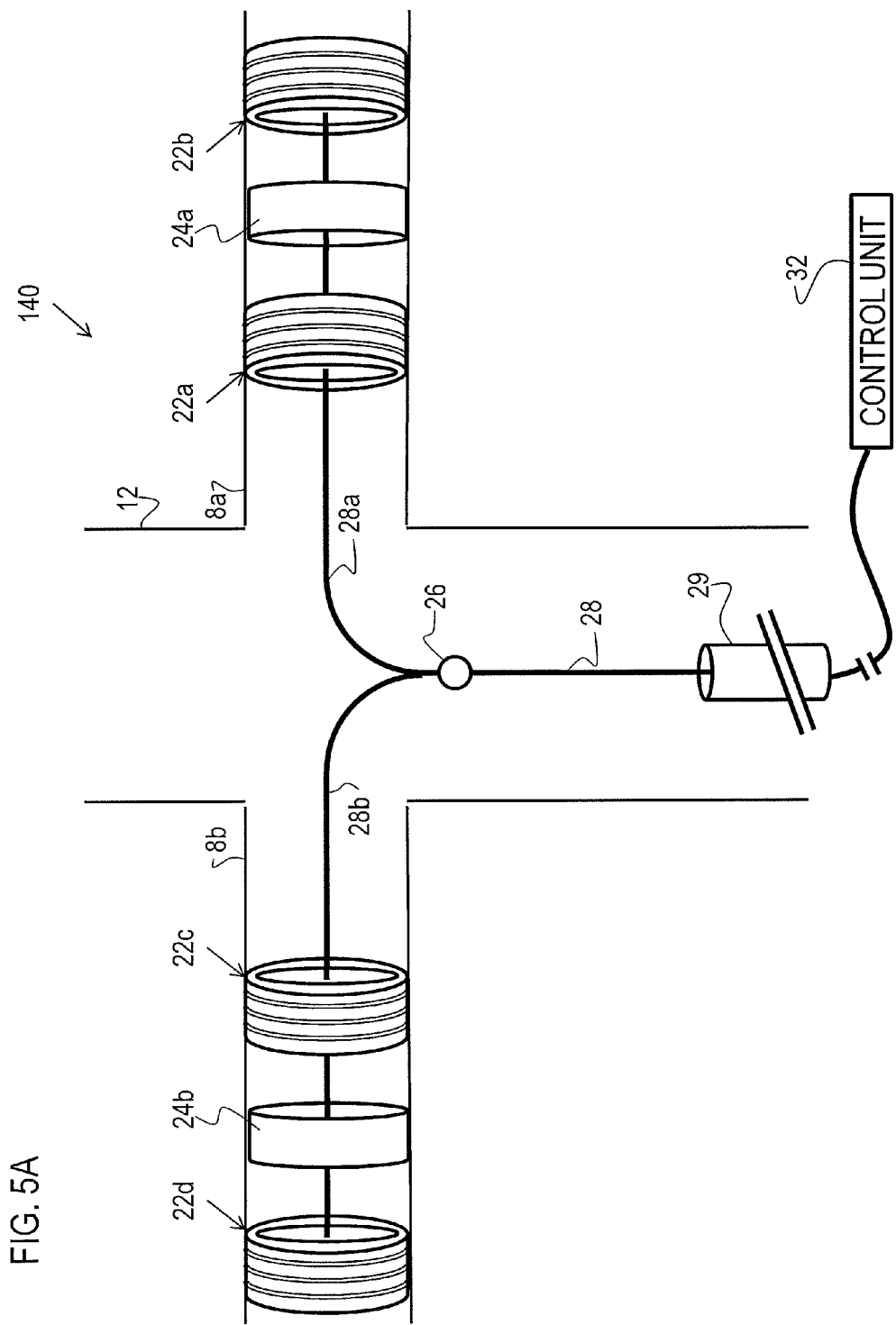
FIGS. 5A-B are schematic illustrations of systems for ablating nerve tissue of at least one renal artery of a subject, in accordance with some applications of the invention.
Figure 5B:
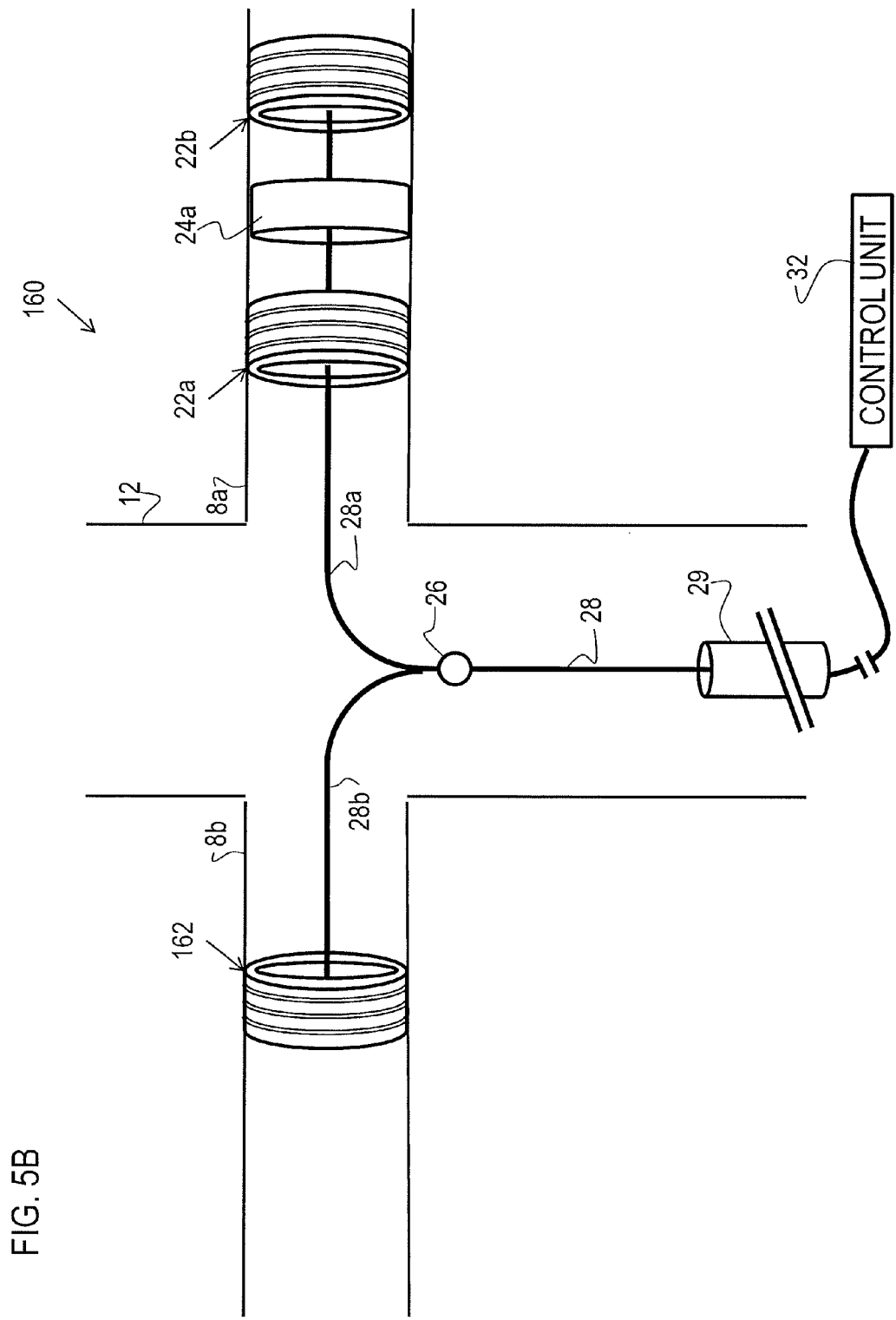

Reference is made to FIGS. 5A-B, which are schematic illustrations of systems for ablating nerve tissue of at least one renal artery of a subject, in accordance with some applications of the invention. For some applications, it is desirable to ablate nerve tissue of both renal arteries 8a and 8b of the subject. For example, it is hypothesized that, for some applications, it is advantageous to ablate the nerve tissue incompletely in both renal arteries (e.g., as opposed to completely ablating the nerve tissue in only one renal artery), so as to retain at least some nerve activity in each renal nerve, e.g., such that each kidney retains at least some blood pressure control. FIG. 5A shows a system 140, comprising two ablation units 24 (i.e., ablation units 24a and 24b), and two pairs of electrode units 22 (one pair comprising electrode units 24a and 24b, and the other pair comprising electrode units 24c and 24d). One ablation unit and one pair of electrode units are disposed in each renal artery, and are configured to ablate nerve tissue of the respective renal artery.

For some applications of the invention, when initiating induced action potentials in nerve tissue of one renal artery, the endogenous action potentials in the nerve tissue of the other renal artery are blocked using the non-ablative blocking current, e.g., so as to reduce obfuscation of any effect seen. Alternatively, induced action potentials are initiated in the nerve tissue of both renal arteries simultaneously. For some applications, it is desirable to perform this blocking and/or initiating in the nerve tissue of the other renal artery even when the nerve tissue of the other renal artery is not to be ablated. For some such applications, system 160, shown in FIG. 5B, is used. System 160 comprises a third electrode unit 162 (which may comprise electrode unit 22c), but typically does not comprise electrode unit 22d or ablating unit 24b. Systems 140 and 160 are typically used as described hereinabove for system 20, mutatis mutandis.

For some applications, longitudinal member 28 of systems 140 and 160 has two distal portions thereof: longitudinal member first distal portion 28a, and longitudinal member first distal portion 28b. That is, for some applications, the distal portion of longitudinal member 28 is bifurcated into distal portions 28a and 28b, each of the distal portions being configured to be advanced into a respective renal artery, as shown in FIGS. 5A-B.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method, comprising:
   transluminally advancing a distal portion of a longitudinal member of a device into a renal artery of a subject;
   operating the device to drive an electrode disposed on the distal portion of the longitudinal member to apply a non-ablative electrical current to nerve tissue of the renal artery;
   receiving (i) a first value, the first value being indicative of a blood pressure of the subject before a start of the application of the current, and (ii) a second value, the second value being indicative of the blood pressure of the subject after a start of the application of the current;
   determining if a difference between the first value and the second value is smaller than a threshold difference; and
   in response to the determining, selecting the subject for performance or non-performance of ablation of a renal artery of the subject, wherein selecting comprises:
   if the determined difference is greater than the threshold difference, operating the device to apply ablation energy to the renal artery; whereas
   if the determined difference is smaller than the threshold difference, withdrawing the longitudinal member from the subject without having applied ablation energy to the renal artery.

2. The method according to claim 1, wherein the non-ablative electrical current is a non-ablative blocking current, and wherein driving the electrode to apply the non-ablative electrical current to the nerve tissue comprises driving the electrode to apply the non-ablative blocking current to the nerve tissue.

3. The method according to claim 1, wherein the non-ablative electrical current is an excitatory current, and wherein driving the electrode to apply the non-ablative electrical current to the nerve tissue comprises driving the electrode to apply the excitatory current to the nerve tissue.

4. The method according to claim 3, wherein driving the electrode to apply the excitatory current to the nerve tissue comprises inducing unidirectional action potentials in the nerve tissue.

5. The method according to claim 1, wherein transluminally advancing the longitudinal member into the renal artery of the subject comprises transfemorally advancing the longitudinal member into the renal artery of the subject.

6. The method according to claim 1, wherein the electrode is a first electrode, and operating the device to drive the electrode to apply the non-ablative current comprises operating the device to drive the non-ablative current between the first electrode and a second electrode disposed on the distal portion of the longitudinal member.

7. The method according to claim 1, wherein the steps of receiving and determining comprise operating the device to (i) receive the first value and the second value, and (ii) determine if the difference is smaller than the threshold difference.

* * * * *